(12) United States Patent
Burwinkel et al.

(10) Patent No.: US 12,310,716 B2
(45) Date of Patent: May 27, 2025

(54) FALL PREDICTION SYSTEM INCLUDING AN ACCESSORY AND METHOD OF USING SAME

(71) Applicant: Starkey Laboratories, Inc., Eden Prairie, MN (US)

(72) Inventors: Justin R. Burwinkel, Eden Prairie, MN (US); Sourav K. Bhunia, Shoreview, MN (US); Jason A. Galster, Minneapolis, MN (US); Buye Xu, Eden Prairie, MN (US); Peter J. Tetrick, Chaska, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 81 days.

(21) Appl. No.: 15/858,680

(22) Filed: Dec. 29, 2017

(65) Prior Publication Data

US 2018/0228405 A1 Aug. 16, 2018

Related U.S. Application Data

(60) Provisional application No. 62/458,436, filed on Feb. 13, 2017.

(51) Int. Cl.
*A61B 5/11* (2006.01)
*A61B 3/113* (2006.01)
(Continued)

(52) U.S. Cl.
CPC ............ *A61B 5/1117* (2013.01); *A61B 3/113* (2013.01); *A61B 5/0002* (2013.01);
(Continued)

(58) Field of Classification Search
None
See application file for complete search history.

(56) References Cited

U.S. PATENT DOCUMENTS 5,913,310 A 6/1999 Brown
6,186,145 B1 2/2001 Brown
(Continued)

FOREIGN PATENT DOCUMENTS

EP 0799597 A1 10/1997
EP 1229508 A1 8/2002
(Continued)

OTHER PUBLICATIONS

Corvera, Jorge, et al., "Evaluation of the Vestibular Autorotation Test (VAT) for Measuring Vestibular Oculomotor Reflex in Clinical Research," 2000, Archives of Medical Research, vol. 31, pp. 384-387 (Year: 2000).*

(Continued)

*Primary Examiner* — Aurelie H Tu
(74) *Attorney, Agent, or Firm* — Pauly, DeVries Smith & Deffner LLC

(57) ABSTRACT

Various embodiments of a fall prediction system and method of using such system are disclosed. The system includes a hearing device for a user, a sensor operatively connected to the hearing device and adapted to detect a characteristic of the user and generate a sensor signal based on the characteristic, an accessory operatively connected to the hearing device, and a controller operatively connected to the hearing device. The controller is adapted to determine a fall risk value based on the sensor signal, compare the fall risk value to a fall risk threshold, and generate a fall prevention output if the fall risk value exceeds the fall risk threshold.

20 Claims, 5 Drawing Sheets

(51) Int. Cl.
  *A61B 5/00*   (2006.01)
  *G01S 19/19*  (2010.01)
  *G08B 21/04*  (2006.01)
  *G16H 40/60*  (2018.01)
  *G16H 50/30*  (2018.01)
  *H04R 25/00*  (2006.01)

(52) U.S. Cl.
  CPC .......... *A61B 5/0004* (2013.01); *A61B 5/1114* (2013.01); *A61B 5/4836* (2013.01); *A61B 5/6815* (2013.01); *A61B 5/6816* (2013.01); *A61B 5/6817* (2013.01); *A61B 5/7275* (2013.01); *A61B 5/7405* (2013.01); *A61B 5/742* (2013.01); *A61B 5/7455* (2013.01); *G01S 19/19* (2013.01); *G08B 21/0446* (2013.01); *G16H 40/60* (2018.01); *G16H 50/30* (2018.01); *H04R 25/305* (2013.01); *H04R 25/554* (2013.01); *A61B 2562/0219* (2013.01); *H04R 2225/55* (2013.01); *H04R 2460/07* (2013.01)

(56) References Cited

U.S. PATENT DOCUMENTS

| | | |
|---|---|---|
| 6,326,918 B1 | 12/2001 | Stewart |
| 6,475,161 B2 | 11/2002 | Teicher et al. |
| 6,568,396 B1 | 5/2003 | Anthony |
| 6,609,523 B1 | 8/2003 | Anthony |
| 6,647,257 B2 | 11/2003 | Owensby |
| D487,409 S | 3/2004 | Philipson |
| 6,758,218 B2 | 7/2004 | Anthony |
| 6,816,878 B1 | 11/2004 | Zimmers et al. |
| 6,836,667 B1 | 12/2004 | Smith, Jr. |
| 7,007,327 B2 | 3/2006 | Ogawa et al. |
| 7,139,820 B1 | 11/2006 | O'Toole, Jr. et al. |
| 7,282,031 B2 | 10/2007 | Hendrich |
| 7,294,107 B2 | 11/2007 | Simon et al. |
| 7,411,493 B2 | 8/2008 | Smith |
| 7,450,954 B2 | 11/2008 | Randall |
| 7,490,611 B2 | 2/2009 | Bromwich |
| 7,602,930 B2 | 10/2009 | Kasztelan |
| 7,612,681 B2 | 11/2009 | Azzaro et al. |
| 7,682,308 B2 | 3/2010 | Hendrich |
| 7,742,774 B2 | 6/2010 | Oh et al. |
| 7,892,180 B2 | 2/2011 | Epley |
| 7,899,621 B2 | 3/2011 | Breed et al. |
| 8,092,398 B2 | 1/2012 | Weinberg et al. |
| 8,150,044 B2 | 4/2012 | Goldstein et al. |
| 8,162,846 B2 | 4/2012 | Epley |
| 8,169,938 B2 | 5/2012 | Duchscher et al. |
| 8,308,665 B2 | 11/2012 | Harry et al. |
| 8,442,245 B2 | 5/2013 | Wurzbacher et al. |
| 8,452,273 B1 | 5/2013 | Khomenko et al. |
| 8,494,507 B1 | 7/2013 | Tedesco et al. |
| 8,559,914 B2 | 10/2013 | Jones |
| 8,585,589 B1 | 11/2013 | Cinberg |
| 8,652,040 B2 | 2/2014 | Leboeuf et al. |
| 8,737,951 B2 | 5/2014 | Jones et al. |
| 9,049,558 B2 | 6/2015 | Jones et al. |
| 9,149,222 B1 | 10/2015 | Zets et al. |
| 9,167,356 B2 | 10/2015 | Higgins et al. |
| 9,179,862 B2 | 11/2015 | Stergiou et al. |
| 9,210,518 B2 | 12/2015 | Zhang |
| 9,216,132 B2 | 12/2015 | Aoki et al. |
| 9,219,964 B2 | 12/2015 | Merks |
| D747,554 S | 1/2016 | Daniel |
| 9,226,706 B2 | 1/2016 | Uehara et al. |
| 9,313,585 B2 | 4/2016 | Lunner |
| 9,392,966 B2 | 7/2016 | Ten Kate |
| 9,414,784 B1 | 8/2016 | Berme et al. |
| 9,426,582 B2 | 8/2016 | Pontoppidan |
| 9,452,101 B2 | 9/2016 | Tomlinson et al. |
| 9,605,390 B2 | 3/2017 | Penland |
| 9,607,498 B2 | 3/2017 | Osorio |
| 9,769,577 B2 | 9/2017 | Shennib |
| 9,848,273 B1 | 12/2017 | Helwani et al. |
| 9,877,668 B1 | 1/2018 | Sarkar et al. |
| 9,918,663 B2 | 3/2018 | Singhatat |
| 9,936,916 B2 | 4/2018 | Sahin |
| 9,999,377 B2 | 6/2018 | Osorio |
| 10,015,579 B2 | 7/2018 | Boesen |
| 10,140,833 B1 | 11/2018 | Jacobson et al. |
| 10,149,798 B2 | 12/2018 | Roth |
| 10,178,970 B2 | 1/2019 | Oddsson et al. |
| 10,242,590 B2 | 3/2019 | Yu |
| 10,258,257 B2 | 4/2019 | Greene |
| 10,262,517 B2 | 4/2019 | Bobda |
| 10,271,790 B2 | 4/2019 | Lee |
| 10,319,209 B2 | 6/2019 | Carlton-Foss |
| 10,587,964 B2 | 3/2020 | Shennib |
| 10,624,559 B2 | 4/2020 | Bhunia et al. |
| 10,799,698 B2 | 10/2020 | Howard |
| 11,277,697 B2 | 3/2022 | Burwinkel et al. |
| 11,559,251 B2 | 1/2023 | Burwinkel et al. |
| 11,638,563 B2 | 5/2023 | Burwinkel et al. |
| 12,149,893 B2 | 11/2024 | Burwinkel et al. |
| 12,254,755 B2 | 3/2025 | Burwinkel et al. |
| 2002/0188217 A1 | 12/2002 | Farwell |
| 2004/0234933 A1 | 11/2004 | Dawson et al. |
| 2005/0046576 A1 | 3/2005 | Julian et al. |
| 2005/0240378 A1 | 10/2005 | Smith et al. |
| 2005/0273017 A1 | 12/2005 | Gordon |
| 2006/0250260 A1* | 11/2006 | Albert ................ G08B 21/0211 340/628 |
| 2006/0251334 A1 | 11/2006 | Oba et al. |
| 2006/0282021 A1* | 12/2006 | DeVaul ................ A61B 5/1117 600/595 |
| 2007/0177103 A1 | 8/2007 | Migliaccio et al. |
| 2007/0197881 A1 | 8/2007 | Wolf et al. |
| 2007/0200927 A1 | 8/2007 | Krenik |
| 2007/0276270 A1 | 11/2007 | Tran |
| 2008/0021731 A1 | 1/2008 | Rodgers |
| 2008/0111677 A1* | 5/2008 | Kolz ................ H04R 25/554 340/539.11 |
| 2008/0129518 A1 | 6/2008 | Carlton-Foss |
| 2008/0146890 A1 | 6/2008 | Leboeuf et al. |
| 2008/0186189 A1 | 8/2008 | Azzaro et al. |
| 2009/0058660 A1 | 3/2009 | Torch |
| 2009/0232357 A1 | 9/2009 | Angell et al. |
| 2009/0240170 A1 | 9/2009 | Rowley et al. |
| 2009/0240172 A1 | 9/2009 | Fernandez et al. |
| 2009/0299622 A1 | 12/2009 | Denaro |
| 2009/0322513 A1* | 12/2009 | Hwang ................ A61B 5/02055 340/539.12 |
| 2010/0010832 A1 | 1/2010 | Boute et al. |
| 2010/0049095 A1 | 2/2010 | Bunn et al. |
| 2010/0075806 A1 | 3/2010 | Montgomery |
| 2010/0141439 A1 | 6/2010 | Lunner |
| 2010/0179389 A1* | 7/2010 | Moroney, III ........ A61B 5/6819 119/857 |
| 2010/0331721 A1 | 12/2010 | Epley |
| 2011/0313315 A1 | 12/2011 | Attias et al. |
| 2012/0075464 A1 | 3/2012 | Derenne et al. |
| 2012/0092156 A1 | 4/2012 | Tran |
| 2012/0101411 A1 | 4/2012 | Hausdorff et al. |
| 2012/0119904 A1 | 5/2012 | Coleman et al. |
| 2012/0219180 A1 | 8/2012 | Mehra |
| 2012/0304767 A1 | 12/2012 | Howard et al. |
| 2013/0065569 A1 | 3/2013 | Leipzig et al. |
| 2013/0091016 A1 | 4/2013 | Shutter |
| 2013/0135097 A1 | 5/2013 | Doezema |
| 2013/0343584 A1 | 12/2013 | Bennett et al. |
| 2013/0343585 A1 | 12/2013 | Bennett et al. |
| 2014/0002586 A1 | 1/2014 | Nourbakhsh |
| 2014/0023216 A1 | 1/2014 | Solum et al. |
| 2014/0024972 A1 | 1/2014 | Greene |
| 2014/0031703 A1* | 1/2014 | Rayner ................ A61B 5/1118 600/484 |
| 2014/0046209 A1 | 2/2014 | Klap et al. |
| 2014/0064528 A1* | 3/2014 | Flood ................ H04R 25/554 381/315 |
| 2014/0074180 A1 | 3/2014 | Heldman et al. |

(56) References Cited

U.S. PATENT DOCUMENTS

| | | |
|---|---|---|
| 2014/0145848 A1 | 5/2014 | Amir |
| 2014/0148733 A1 | 5/2014 | Stone et al. |
| 2014/0257051 A1 | 9/2014 | Cam et al. |
| 2014/0266988 A1 | 9/2014 | Fisher et al. |
| 2014/0276238 A1 | 9/2014 | Osorio |
| 2014/0341408 A1* | 11/2014 | Varghese ............ H04R 25/554 381/315 |
| 2015/0018724 A1 | 1/2015 | Hsu et al. |
| 2015/0040685 A1 | 2/2015 | Nicholson et al. |
| 2015/0106026 A1* | 4/2015 | Goldstein .......... A61B 5/14542 702/19 |
| 2015/0112151 A1 | 4/2015 | Muhsin et al. |
| 2015/0112162 A1 | 4/2015 | Wilmink |
| 2015/0164383 A1 | 6/2015 | Varsavsky et al. |
| 2015/0170296 A1 | 6/2015 | Kautz et al. |
| 2015/0196231 A1 | 7/2015 | Ziaie et al. |
| 2015/0209212 A1 | 7/2015 | Duguid |
| 2015/0226621 A1 | 8/2015 | Zhu et al. |
| 2015/0257662 A1 | 9/2015 | Lee et al. |
| 2015/0269824 A1* | 9/2015 | Zhang ................. A61B 5/746 340/539.12 |
| 2015/0319546 A1 | 11/2015 | Sprague |
| 2015/0351690 A1 | 12/2015 | Toth et al. |
| 2016/0015289 A1 | 1/2016 | Simon et al. |
| 2016/0029938 A1 | 2/2016 | Shudo |
| 2016/0033280 A1 | 2/2016 | Moore et al. |
| 2016/0057550 A1 | 2/2016 | Shennib |
| 2016/0070122 A1 | 3/2016 | Sales et al. |
| 2016/0100776 A1* | 4/2016 | Najafi ................. A61B 5/7225 600/595 |
| 2016/0106346 A1 | 4/2016 | Benzel et al. |
| 2016/0155312 A1 | 6/2016 | Osorio |
| 2016/0166190 A1 | 6/2016 | Publicover et al. |
| 2016/0262608 A1 | 9/2016 | Krueger |
| 2016/0263437 A1 | 9/2016 | Kow et al. |
| 2016/0275805 A1 | 9/2016 | Reichow |
| 2016/0295978 A1 | 10/2016 | Hyde et al. |
| 2017/0000387 A1 | 1/2017 | Forth et al. |
| 2017/0006931 A1 | 1/2017 | Guez et al. |
| 2017/0007147 A1 | 1/2017 | Hasegawa |
| 2017/0055917 A1 | 3/2017 | Stone et al. |
| 2017/0071532 A1 | 3/2017 | Greco |
| 2017/0112671 A1 | 4/2017 | Goldstein |
| 2017/0113057 A1 | 4/2017 | Goodall et al. |
| 2017/0116846 A1 | 4/2017 | Wengrovitz et al. |
| 2017/0127196 A1* | 5/2017 | Blum .................... H04R 25/602 |
| 2017/0140637 A1 | 5/2017 | Thurlow et al. |
| 2017/0156965 A1 | 6/2017 | Geisinger et al. |
| 2017/0169716 A1 | 6/2017 | Super et al. |
| 2017/0172465 A1 | 6/2017 | Osorio |
| 2017/0188895 A1 | 7/2017 | Nathan |
| 2017/0197115 A1 | 7/2017 | Cook et al. |
| 2017/0229041 A1 | 8/2017 | Reichow et al. |
| 2017/0273616 A1 | 9/2017 | Yang et al. |
| 2017/0274219 A1 | 9/2017 | Ernst et al. |
| 2017/0291065 A1 | 10/2017 | Klopman |
| 2017/0352240 A1 | 12/2017 | Carlton-Foss |
| 2017/0358195 A1 | 12/2017 | Bobda |
| 2017/0358241 A1 | 12/2017 | Wexler et al. |
| 2017/0360364 A1 | 12/2017 | Heasman et al. |
| 2018/0000385 A1 | 1/2018 | Heaton et al. |
| 2018/0092572 A1 | 4/2018 | Sanchez et al. |
| 2018/0093121 A1 | 4/2018 | Matsuura et al. |
| 2018/0110466 A1 | 4/2018 | Ralston |
| 2018/0132757 A1 | 5/2018 | Kong et al. |
| 2018/0177436 A1 | 6/2018 | Chang et al. |
| 2018/0202813 A1 | 7/2018 | Belt et al. |
| 2018/0233028 A1 | 8/2018 | Rhoads et al. |
| 2018/0234781 A1 | 8/2018 | Stewart et al. |
| 2018/0242859 A1* | 8/2018 | LeBoeuf ................ G16H 50/30 |
| 2018/0250494 A1 | 9/2018 | Hanbury |
| 2018/0279915 A1 | 10/2018 | Huang et al. |
| 2018/0279919 A1 | 10/2018 | Bansbach et al. |
| 2018/0289287 A1 | 10/2018 | Sio et al. |
| 2018/0336773 A1 | 11/2018 | Hanson et al. |
| 2018/0341582 A1 | 11/2018 | Moon et al. |
| 2018/0343527 A1 | 11/2018 | Edwards |
| 2018/0373841 A1 | 12/2018 | Harpale |
| 2019/0008435 A1 | 1/2019 | Cakmak |
| 2019/0015046 A1* | 1/2019 | Whitehouse ......... A61B 5/6804 |
| 2019/0043610 A1 | 2/2019 | Vaughan |
| 2019/0066477 A1 | 2/2019 | Peyrard |
| 2019/0103007 A1 | 4/2019 | Tan et al. |
| 2019/0117121 A1 | 4/2019 | Kutina et al. |
| 2019/0246890 A1 | 8/2019 | Kerasidis et al. |
| 2020/0138364 A1 | 5/2020 | Fabry et al. |
| 2020/0143703 A1 | 5/2020 | Fabry et al. |
| 2020/0187829 A1 | 6/2020 | Mohamed Elmahdy et al. |
| 2020/0205746 A1 | 7/2020 | Burwinkel et al. |
| 2020/0219373 A1 | 7/2020 | Stut et al. |
| 2020/0236479 A1 | 7/2020 | Burwinkel et al. |
| 2020/0245869 A1 | 8/2020 | Sivan et al. |
| 2020/0268260 A1 | 8/2020 | Tran |
| 2020/0273566 A1 | 8/2020 | Bhowmik et al. |
| 2022/0031195 A1 | 2/2022 | Hu et al. |
| 2022/0034495 A1 | 2/2022 | Chen et al. |
| 2022/0248153 A1 | 8/2022 | Burwinkel et al. |
| 2022/0248970 A1 | 8/2022 | Burwinkel et al. |
| 2022/0361787 A1 | 11/2022 | Burwinkel et al. |
| 2023/0397891 A1 | 12/2023 | Talebanpour et al. |
| 2023/0404490 A1 | 12/2023 | Burwinkel et al. |
| 2024/0000315 A1 | 1/2024 | Shahar et al. |

FOREIGN PATENT DOCUMENTS

| | | |
|---|---|---|
| EP | 1628504 A2 | 2/2006 |
| EP | 2104366 A2 | 9/2009 |
| EP | 2700907 | 2/2014 |
| EP | 2725818 | 4/2014 |
| EP | 3075306 | 10/2016 |
| EP | 3131027 | 2/2017 |
| EP | 1983896 | 6/2017 |
| EP | 3246888 | 11/2017 |
| EP | 3346402 | 7/2018 |
| EP | 3402218 | 11/2018 |
| EP | 3591990 | 1/2020 |
| EP | 3669765 | 6/2020 |
| WO | 2008143908 | 11/2008 |
| WO | WO 2009/053184 A1 | 4/2009 |
| WO | WO 2010/046504 A2 | 4/2010 |
| WO | WO 2010/049543 A2 | 5/2010 |
| WO | WO 2010/108287 A1 | 9/2010 |
| WO | WO 2012/083102 A1 | 6/2012 |
| WO | 2015164456 | 10/2015 |
| WO | 2016097746 | 6/2016 |
| WO | WO 2016/088027 A1 | 6/2016 |
| WO | WO 2016/110804 A1 | 7/2016 |
| WO | WO 2016/123129 A1 | 8/2016 |
| WO | 2017023864 | 2/2017 |
| WO | 2018093765 | 5/2018 |
| WO | 2018127851 | 7/2018 |
| WO | 2018223505 | 12/2018 |
| WO | 2019073473 | 4/2019 |
| WO | 2019086997 | 5/2019 |
| WO | 2020097353 | 5/2020 |
| WO | 2020097355 | 5/2020 |
| WO | 2020124022 | 6/2020 |
| WO | 2020139850 | 7/2020 |
| WO | 2020206155 | 10/2020 |
| WO | 2021016094 | 1/2021 |
| WO | 2022094089 | 5/2022 |
| WO | 2022103954 | 5/2022 |

OTHER PUBLICATIONS

"International Preliminary Report on Patentability," for PCT Application No. PCT/US2017/069026 mailed Aug. 22, 2019 (9 pages).
"International Preliminary Report on Patentability," for PCT Application No. PCT/US2017/0690365 mailed Aug. 22, 2019 (9 pages).
"International Preliminary Report on Patentability," for PCT Application No. PCT/US2018/017944 mailed Aug. 22, 2019 (7 pages).
"Notice of Allowance," for U.S. Appl. No. 15/858,630 mailed Jul. 22, 2019 (10 pages).

(56) References Cited

OTHER PUBLICATIONS

"Response to Final Office Action," for U.S. Appl. No. 15/858,630, filed Jun. 20, 2019 (11 pages).
U.S. Appl. No. 15/589,298, filed May 8, 2017, Burwinkel et al.
U.S. Appl. No. 15/858,630, filed Dec. 29, 2017, Bhunia et al.
U.S. Appl. No. 15/895,311, filed Feb. 13, 2018, Burwinkel et al.
Barber & Stockwell, "Manual of Electronystagmography," 1980, C.V. Mosby Company, St. Louis, Missouri, Cover page, copyright page, and table of contents; total of 3 pages.
Buatois et al., "Posturography and risk of recurrent falls in healthy non-institutionalized persons aged over 65," *Gerontology*, 2006; 52(6):345-352.
Da Costa et al., "Can falls risk prediction tools correctly identify fall-prone elderly rehabilitation inpatients? A systematic review and meta-analysis," *PLoS ONE*, 2012; 7(7):e41061.
El Miedany et al., "Falls risk assessment score (FRAS): Time to rethink," *Journal of Clinical Gerontology & Geriatrics*, 2011; 2(1):21-26.
Horak, "Postural orientation and equilibrium: what do we need to know about neural control of balance to prevent falls?" *Age and Ageing*, 2006; 35-S2:ii7-ii11.
Howcroft et al., "Understanding dynamic stability from pelvis accelerometer data and the relationship to balance and mobility in transtibial amputees," *Gait Posture*, 2015; 41(3):808-812.
Howcroft et al., "Review of fall risk assessment in geriatric populations using inertial sensors," *J Neuroeng Rehab*, 2013; 10:91.
International Search Report and Written Opinion for PCT application No. PCT/US2017/069026, Apr. 3, 2018, 14 pages.
International Search Report and Written Opinion for PCT application No. PCT/US2017/069035, Apr. 3, 2018, 14 pages.
International Search Report and Written Opinion for PCT application No. PCT/US2018/017944, Apr. 26, 2018, 10 pages.
Marschollek et al., "Predicting in-patient falls in a geriatric clinic: a clinical study combining assessment data and simple sensory gait measurements," *Z Gerontol Geriatr*, 2009; 42(4):317-321.
Oliver, "Falls risk-prediction tools for hospital inpatients. Time to put them to bed?" *Age and Ageing*, 2008; 37:248-250.
Path VU Mobile App, Pathway Accessibility Solutions, Inc., Pittsburgh, Pennsylvania [retrieved on Jun. 19, 2018. Retrieved from the Internet:<URL: http://www.pathvu.com/>; 6 pgs.
Rumalla et al., "The effect of hearing aids on postural stability," *Laryngoscope*, 2015; 125(3):720-723.
Viikki, "Machine Learning on Otoneurological Data: Decision Trees for Vertigo Diseases," Academic Dissertation, University of Tampere, Finland, 2002; 84 pages.
Yang et al., "Fall risk assessment and early-warning for toddler behaviors at home," *Sensors*, 2013; 13:16985-17005.
Klenk et al., "Conceptualizing a Dynamic Fall Risk Model Including Intrinsic Risks and Exposures," *JAMDA*, 2017; 18:921-927.
"Final Office Action," for U.S. Appl. No. 15/895,311 mailed Jul. 17, 2020 (18 pages).
Hendrich, Ann et al., "Hospital Falls: Development of a Predictive Model for Clinical Practice," Applied Nursing Research, vol. 8, No. 3 Aug. 1995: pp. 129-139 (11 pages).
Hendrich, Ann L. et al., "Validation of the Hendrich II Fall Risk Model: A Large Concurrent Case/Control Study of Hospitalized Patients," Applied Nursing Research, vol. 16, No. 1 Feb. 2003: pp. 9-21 (13 pages).
"International Search Report and Written Opinion," for PCT Application No. PCT/US2019/066358 mailed Jun. 23, 2020 (18 pages).
"International Search Report and Written Opinion," for PCT Application No. PCT/US2019/068397 mailed Apr. 14, 2020 (14 pages).
"Invitation to Pay Additional Fees and, Where Applicable, Protest Fee," for PCT Application No. PCT/US2019/066358 mailed Mar. 5, 2020 (12 pages).
"Non-Final Office Action," for U.S. Appl. No. 15/895,311 mailed Mar. 17, 2020 (26 pages).
"Response to Final Office Action," for U.S. Appl. No. 15/895,311, filed Oct. 19, 2020 (13 pages).

"Response to Non-Final Office Action," for U.S. Appl. No. 15/895,311, filed Jun. 12, 2020 (10 pages).
Leake, Jason L. "Fall Detectors for People with Dementia," University of Bath Student Thesis, Jun. 2016 (364 pages).
"Non-Final Office Action," for U.S. Appl. No. 15/895,311 mailed Feb. 23, 2021 (12 pages).
"Response to Non-Final Office Action," for U.S. Appl. No. 15/895,311, filed Mar. 17, 2021 (7 pages).
"Final Office Action," for U.S. Appl. No. 15/895,311 mailed Apr. 13, 2021 (9 pages).
"International Preliminary Report on Patentability," for PCT Application No. PCT/US2019/066358 mailed Jun. 24, 2021 (12 pages).
"International Preliminary Report on Patentability," for PCT Application No. PCT/US2019/068397 mailed Jul. 8, 2021 (9 pages).
"Non-Final Office Action," for U.S. Appl. No. 16/714,339 mailed May 17, 2021 (34 pages).
"Response to Final Office Action," for U.S. Appl. No. 15/895,311, filed Sep. 13, 2021 (7 pages).
"Response to Non-Final Office Action," for U.S. Appl. No. 16/714,339, filed Sep. 15, 2021 (6 pages).
"European Search Report," for European Patent Application No. 19212657.1 mailed Feb. 14, 2020 (10 pages).
"International Preliminary Report on Patentability," for PCT Application No. PCT/US2020/026435 mailed Oct. 14, 2021 (8 pages).
"International Search Report and Written Opinion," for PCT Application No. PCT/US2020/026435 mailed Jul. 9, 2020 (12 pages).
"Non-Final Office Action," for U.S. Appl. No. 16/725,766 mailed Oct. 8, 2021 (30 pages).
"Notice of Allowance," for U.S. Appl. No. 16/714,339 mailed Nov. 2, 2021 (13 pages).
Zheng, et al. "Effect of postural changes on lower limb blood volume, detected with non-invasive photoplethysmography," Journal of Medical Engineering & Technology, vol. 32, No. 5, Sep./Oct. 2008, pp. 358-364 (7 pages).
"Communication Pursuant to Article 94(3) EPC," for European Patent Application No. 17838110.9 mailed Feb. 1, 2022 (8 pages).
"Final Office Action," for U.S. Appl. No. 16/725,766 mailed Mar. 7, 2022 (19 pages).
"International Search Report and Written Opinion," for PCT Application No. PCT/US2021/057064 mailed Feb. 10, 2022 (15 pages).
"Non-Final Office Action," for U.S. Appl. No. 15/895,311 mailed Feb. 9, 2022 (17 pages).
"Non-Final Office Action," for U.S. Appl. No. 16/725,766 mailed Jun. 24, 2022 (16 pages).
"Response to Final Office Action," for U.S. Appl. No. 16/725,766 filed Jun. 7, 2022 (8 pages).
"Response to Non-Final Office Action," for U.S. Appl. No. 15/895,311, filed Jun. 9, 2022 (9 pages).
"Final Office Action," for U.S. Appl. No. 15/895,311 mailed Jul. 18, 2022 (15 pages).
"Response to Final Office Action," for U.S. Appl. No. 15/895,311, filed Oct. 18, 2022 (10 pages).
"Response to Non-Final Office Action," for U.S. Appl. No. 16/725,766, filed Sep. 23, 2022 (9 pages).
Wen, Jiaqu, et al. "We Help You Watch Your Steps: Unobtrusive Alertness System for Pedestrian Mobile Phone Users," 2015, IEEE International Conference on Pervasive Computing and Communications (PerCom), pp. 105-113 (9 pages).
"Non-Final Office Action," for U.S. Appl. No. 15/895,311 mailed Dec. 28, 2022 (21 pages).
"Notice of Allowance," for U.S. Appl. No. 16/725,766 mailed Dec. 23, 2022 (12 pages).
"Response to Non-Final Office Action," for U.S. Appl. No. 15/895,311, filed Mar. 20, 2023 (15 pages).
"Communication Pursuant to Article 94(3) EPC," for European Patent Application No. 19839777.0 mailed Aug. 18, 2023 (5 pages).
"Communication Pursuant to Article 94(3) EPC," for European Patent Application No. 20754071.1 mailed Aug. 11, 2023 (5 pages).
"Final Office Action," for U.S. Appl. No. 15/895,311 mailed May 8, 2023 (25 pages).
"International Preliminary Report on Patentability," for PCT Application No. PCT/US2020/042571 mailed Feb. 3, 2022 (14 pages).

(56) References Cited

OTHER PUBLICATIONS

"International Preliminary Report on Patentability," for PCT Application No. PCT/US2021/057064 mailed May 11, 2023 (11 pages).
"International Preliminary Report on Patentability," for PCT Application No. PCT/US2021/058971 mailed May 25, 2023 (12 pages).
"International Search Report and Written Opinion," for PCT Application No. PCT/US2019/060296 mailed Apr. 14, 2020 (14 pages).
"International Search Report and Written Opinion," for PCT Application No. PCT/US2019/060298 mailed Apr. 28, 2020 (20 pages).
"International Search Report and Written Opinion," for PCT Application No. PCT/US2020/042571 mailed Nov. 25, 2020 (20 pages).
"International Search Report and Written Opinion," for PCT Application No. PCT/US2021/058971 mailed Mar. 3, 2022 (17 pages).
"Invitation to Pay Additional Fees," for PCT Application No. PCT/US2020/042571 mailed Sep. 16, 2020 (15 pages).
"Non-Final Office Action," for U.S. Appl. No. 15/589,298 mailed Jan. 2, 2019 (8 pages).
"Non-Final Office Action," for U.S. Appl. No. 15/589,298 mailed Jul. 11, 2019 (13 pages).
"Non-Final Office Action," for U.S. Appl. No. 15/589,298 mailed May 19, 2020 (15 pages).
"Non-Final Office Action," for U.S. Appl. No. 17/673,461 mailed Sep. 27, 2023 (43 pages).
"Notice of Allowance," for U.S. Appl. No. 15/589,298 mailed Jan. 22, 2020 (12 pages).
"Response to Final Office Action," for U.S. Appl. No. 15/895,311, filed Jul. 28, 2023 (16 pages).
"Response to Non-Final Office Action," for U.S. Appl. No. 15/589,298, filed Apr. 1, 2019 (8 pages).
"Response to Non-Final Office Action," for U.S. Appl. No. 15/589,298, filed Aug. 19, 2020 (14 pages).
"Response to Non-Final Office Action," for U.S. Appl. No. 15/589,298, filed Oct. 3, 2019 (12 pages).
"Understanding Heart Disease," WebMD Heart Disease Guide Written by WebMD Editorial Contributors and medically reviewed by James Beckerman, published at https://www.webmd.com/heart-disease/understanding-heart-disease-symptoms at least as early as Mar. 2007 (10 pages).
EP Search Report dated Oct. 8, 2018 from EP App. No. 18171323.1, 10 pages.
Choi, W. J., et al. "Effect of Neck Flexor Muscle Activation on Impact Velocity of the Head During Backward Falls in Young Adults," Clinical Biomechanics 49 (2017), pp. 28-33.
Coburn, Courtney, et al ."The Comfort Bud: Designed with Patients in Mind," Starkey Hearing Technologies Product Sheet, 2017 (2 pages).
Farrell, Lisa, et al. "Vestibular Rehabilitation: An Effective, Evidence-Based Treatment," Vestibular Disorders Association 2015 (11 pages).
Raj, Rahul, et al. "Factors correlating with delayed trauma center admission following traumatic brain injury," Scandinavian Journal of Trauma, Resuscitation and Emergency Medicine 2013, 21:67 (9 pages).
Salisbury, Joseph P., et al. "Patient Engagement Platform for Remote Monitoring of Vestibular Rehabilitation with Applications in Concussion Management and Elderly Fall Prevention," 2018 IEEE International Conference on Healthcare Informatics, pp. 422-423.
Tinetti, Mary E., et al. "Antihypertensive Medications and Serious Fall Injuries in a Nationally Representative Sample of Older Adults," JAMA Intern. Med. Apr. 2014; 174(4): 588-595 (16 pages).
"Final Office Action," for U.S. Appl. No. 15/895,311 mailed Mar. 12, 2024 (15 pages).
"Final Office Action," for U.S. Appl. No. 17/673,461 mailed Mar. 13, 2024 (22 pages).
"Non-Final Office Action," for U.S. Appl. No. 15/895,311 mailed Oct. 12, 2023 (13 pages).
"Non-Final Office Action," for U.S. Appl. No. 17/600,370 mailed Feb. 28, 2024 (43 pages).
"Response to Non-Final Office Action," for U.S. Appl. No. 15/895,311, filed Jan. 12, 2024 (9 pages).
"Response to Non-Final Office Action," for U.S. Appl. No. 17/673,461, filed Dec. 27, 2023 (11 pages).
"Non-Final Office Action," for U.S. Appl. No. 18/139,671 mailed Apr. 11, 2024 (42 pages).
"Response to Final Office Action," for U.S. Appl. No. 15/895,311, filed Jun. 12, 2024 (8 pages).
"Response to Final Office Action," for U.S. Appl. No. 17/673,461, filed Jun. 13, 2024 (10 pages).
"Response to Non-Final Office Action," for U.S. Appl. No. 17/600,370, filed Jun. 28, 2024 (13 pages).
"Notice of Allowance," for U.S. Appl. No. 15/895,311 mailed Aug. 14, 2024 (17 pages).
"Final Office Action," mailed Jul. 22, 2024, for U.S. Appl. No. 18/139,671 21 pages.
"Notice of Allowance," for U.S. Appl. No. 17/673,461 mailed Jul. 12, 2024 (14 pages).
"Response to Non-Final Office Action," for U.S. Appl. No. 18/139,671, filed Jul. 3, 2024 (10 pages).
"Non-Final Office Action," for U.S. Appl. No. 18/139,671 mailed Nov. 18, 2024 (24 pages).
"Final Office Action," for U.S. Appl. No. 17/600,370 mailed Oct. 21, 2024 (34 pages).
"Response to Final Office Action" Response to Final Office Action, for U.S. Appl. No. 18/139,671, filed Oct. 10, 2024 (11 pages).
"Non-Final Office Action," for U.S. Appl. No. 17/628,436 mailed Sep. 29, 2024 (56 pages).
"Non-Final Office Action," for U.S. Appl. No. 17/600,370 mailed Feb. 6, 2025 (39 pages).
"Response to Final Office Action," for U.S. Appl. No. 17/600,370 filed Jan. 17, 2025 (13 pages).
"Response to Non-Final Office Action," for U.S. Appl. No. 17/628,436 filed Dec. 20, 2024 (12 pages).
"Response to Non-Final Office Action," for U.S. Appl. No. 18/139,671 filed Feb. 12, 2025 (11 pages).
"Final Office Action," for U.S. Appl. No. 17/628,436 mailed Apr. 2, 2025 (25 pages).
"Final Office Action," for U.S. Appl. No. 18/139,671 mailed Mar. 18, 2025 (24 pages).
"Response to Non-Final Office Action," for U.S. Appl. No. 17/600,370, filed on Apr. 28, 2025 (13 pages).

\* cited by examiner

FALL PREDICTION SYSTEM INCLUDING AN ACCESSORY AND METHOD OF USING SAME

CROSS-REFERENCE TO RELATED APPLICATION

This application claims priority to U.S. Provisional Patent Application No. 62/458,436, filed Feb. 13, 2017, which is incorporated herein by reference.

BACKGROUND

Maintaining postural control and preventing a fall are of importance for the elderly. Falls are the second leading cause of accidental or unintentional injury deaths worldwide, and are especially prevalent in the elderly. Currently, individuals are often inadequately prepared to protect themselves from falls or other serious injuries as the onset of such events may come without perceptible warning. Further, maintaining postural equilibrium, i.e., prevention of a fall, involves stabilization of the body's center of mass during both self-initiated and externally triggered disturbances to postural stability during normal daily activities. Maintaining such equilibrium can be accomplished by limiting the motion of the center of mass within the base of support formed by and around the feet. Postural equilibrium is maintained through multisensory inputs. For example, loss of sensory input in the feet due to neuropathy can increase the risk of a fall, even though the necessary motor control for a corrective action of repositioning the feet may still be intact.

Differential diagnosis of balance-related conditions often takes weeks or longer and can become especially costly to perform. A typical balance-related evaluation can last 1-2 hours and require a clinician to induce symptoms of imbalance, which can be especially uncomfortable for patients as they may begin to feel dizzy and nauseous. Further, many patients do not have complete recollection of the events leading up to and during a period of spontaneous imbalance or a fall. In addition, adherence to postural training provided by healthcare specialists is not easily monitored during normal daily activities outside of the training facility.

SUMMARY

In general, the present disclosure provides various embodiments of a fall prediction system and a method of utilizing such a system. The fall prediction system can include a hearing device, one or more sensors operatively connected to the device, and one or more accessories also operatively connected to the hearing device. The one or more sensors are adapted to detect one or more characteristics of a user of the device and generate one or more sensor signals based on the characteristic. The characteristic can be any suitable characteristic of the user, including at least one of a physiological characteristic and an environmental characteristic of the user. A controller of the system can be adapted to determine a fall risk value based on the sensor signal, compare the fall risk value to a fall risk threshold, and generate a fall prevention signal if the fall risk value exceeds the fall risk threshold.

In one aspect, the present disclosure provides a fall prediction system that includes a hearing device for a user, a sensor operatively connected to the hearing device and adapted to detect a characteristic of the user and generate a sensor signal based on the characteristic, where the characteristic includes at least one of a physiological characteristic and an environmental characteristic of the user; an accessory operatively connected to the hearing device; and a controller operatively connected to the hearing device. The controller is adapted to determine a fall risk value based on the sensor signal, compare the fall risk value to a fall risk threshold, and generate a fall prevention output if the fall risk value exceeds the fall risk threshold.

In another aspect, the present disclosure provides a method that includes detecting a characteristic of a user of a fall prediction system with a sensor, where the fall prediction system includes a hearing device and an accessory, and further where the characteristic includes at least one of a physiological characteristic and an environmental characteristic; and determining a fall risk value based on the detected characteristic. The method further includes determining a fall risk threshold, and comparing the fall risk value to the fall risk threshold.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
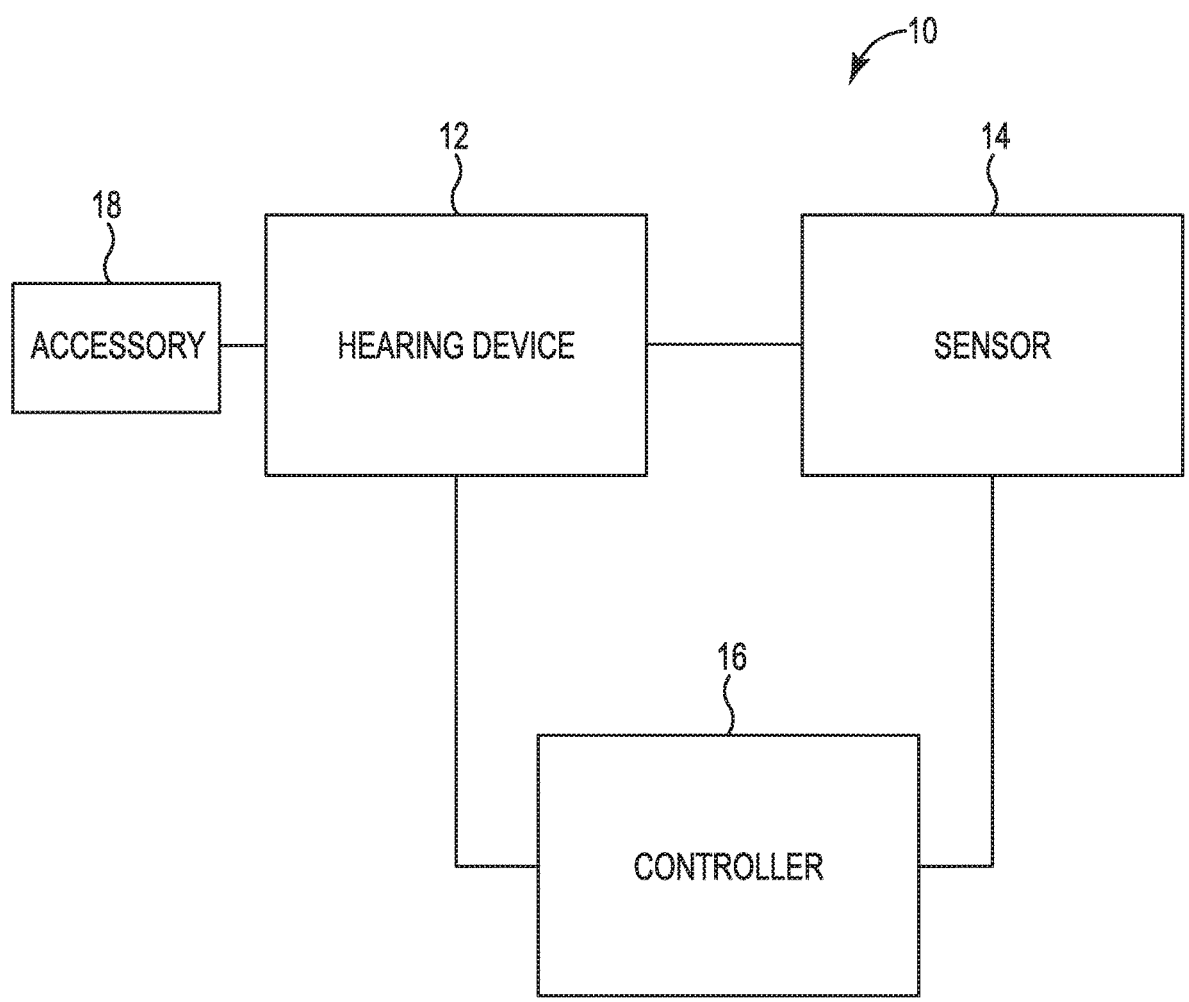
FIG. 1 is a schematic cross-section view of one embodiment of a fall prediction system.

In general, the present disclosure provides various embodiments of a fall prediction system and a method of utilizing such system. The fall prediction system can include a hearing device, one or more sensors operatively connected to the device, and one or more accessories also operatively connected to the hearing device. The one or more sensors are adapted to detect one or more characteristics of a user of the device and generate one or more sensor signals based on the characteristic. The characteristic can be any suitable characteristic of the user, including at least one of a physiological characteristic and an environmental characteristic. A controller of the system can be adapted to determine a fall risk value based on the sensor signal, compare the fall risk value to a fall risk threshold, and generate a fall prevention signal if the fall risk value exceeds the fall risk threshold. In one or more embodiments, the controller can also be adapted to determine the fall risk value based on the sensor signal and data or information from the accessory.

The fall prediction systems and methods described herein can be utilized to determine whether a user of such system or systems may have an increased probability of a fall. Further, one or more embodiments of a fall prediction system described herein can provide one or more outputs that can prevent the user of the system from falling. One or more embodiments of a fall prediction system described herein can also be utilized to determine whether the user of the device has experienced a fall.

Any suitable technique or techniques can be utilized with the described embodiments of fall prediction systems. For example, in one or more embodiments, a fall prediction system can include one or more sensors to detect, predict, and prevent its user from falling. Such sensors can include, e.g., one or more of a microphone, a loudspeaker, an accelerometer, a barometer, a magnetometer, a gyroscope, an electrode sensor, and an optical sensor. In one or more embodiments, an accelerometer can be utilized with one or both of a magnetometer and gyroscope for fall prediction and detection. For example, detection of a fall of the user can be accomplished by detecting, e.g., the speed of change of posture while the relative orientation of both the system and the user remain the same, and body rotation of the user, etc. Postural stability can include detection of a fluctuation in a magnitude and direction of acceleration as the user goes about daily activities. Such detection can also include day-to-day variations in heart rate during comparable activities. Both the long-term and short-term risks of a fall can be predicted. In general, the long-term risk is the probability of falling based on the user's long-term history of health, motion, physiological patterns, etc. Further, the short-term fall risk can indicate the fall risk at the moment based on the current physiological status of the user and the environment proximate the user (e.g., slippery floors).

In one or more embodiments, the fall prediction system can include one or more sensors that measure eye movement (i.e., electrooculography (EOG) measurements). For example, the system can include one or more EOG sensors for the tracking of eye movement and nystagmus. In one or more embodiments, the system can also include a positional sensor that may be utilized to correlate EOG sensor data. Data from the EOG sensors and positional sensors can be utilized to detect peripheral vestibular asymmetry (which can cause nystagmus and feelings of imbalance/dizziness to occur).

Parallel positional sensors that can be provided by a fall prediction system and that include a binaural set of hearing devices can also be used to detect falls. Further, the use of two separate, but parallel, positional sensors can provide a redundant system that can prevent false-positive fall detection.

Any suitable fall prediction system or device can be utilized for fall prediction, prevention, and/or detection. For example, FIG. 1 is a schematic cross-section view of one embodiment of a fall prediction system 10. The fall prediction system 10 includes a hearing device 12 for a user, a sensor 14 operatively connected to the hearing device, an accessory 18 operatively connected to the hearing device, and a controller 16 operatively connected to at least one of the hearing device, the accessory and the sensor. As used herein, the term "operatively connected" means that an element or component can be connected to another element or component using any suitable technique or techniques such that information can be shared between such components. In one or more embodiments, the sensor 14 and the accessory 18 can be operatively connected to the hearing device 12 by a wire or cable, wirelessly using any suitable wireless protocol, optically, etc.

The sensor 14 is adapted to detect a characteristic of the user, e.g., at least one of a physiological characteristic and an environmental characteristic, and generate a sensor signal based on such characteristic. In one or more embodiments, the controller 16 is adapted to determine a fall risk value based on the sensor signal, compare the fall risk value to a fall risk threshold, and generate a fall prevention output if the fall risk value exceeds the fall risk threshold as is further described herein. In one or more embodiments, the controller 16 can be adapted to determine a second fall risk value based on the sensor signal, compare the second fall risk value to a second fall risk threshold, and generate a second fall prevention output if the second fall risk value exceeds the second fall risk threshold. In one or more embodiments, the controller 16 can be adapted to determine any suitable number of risk values and compare those values to any suitable number of fall risk thresholds.

The system 10 can include any suitable hearing device 12 for a user, including but not limited to, a wearable hearing device such as headphones. In one or more embodiments, the hearing device can include a hearing aid such as behind-the-ear (BTE), in-the-ear (ITE), in-the-canal (ITC), or completely-in-the-canal (CIC) type hearing aid. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user. Such devices are also known as receiver-in-the-canal (RIC) or receiver-in-the-ear (RITE) hearing devices. In one or more embodiments, the hearing device 12 can include a cochlear implant (including its processor) or a bone-conduction or otherwise osseointegrated hearing device. It is understood that other hearing devices not expressly stated herein may fall within the scope of the present subject matter. While depicted as including one hearing device 12, the system 10 can include two or more hearing devices. For example, in one or more embodiments, the system 10 can include a left hearing device that is adapted to be acoustically connected to the user's left ear and a right hearing device that is adapted to be acoustically connected to the user's right ear.

Figure 2:
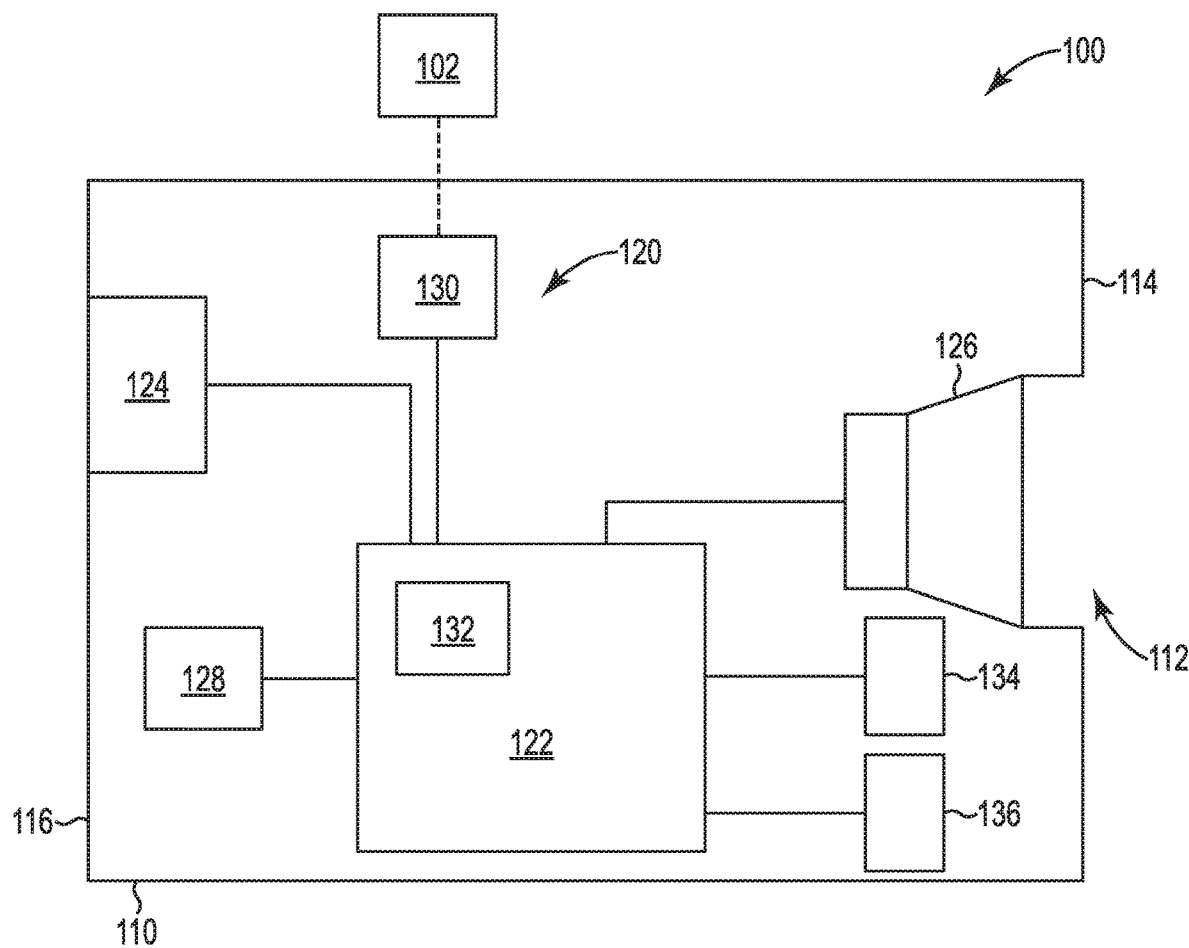
FIG. 2 is a schematic cross-section view of one embodiment of a hearing device that can be utilized with the fall prediction system of FIG. 1.

The hearing device 12 can include any suitable hearing assistance components. For example, FIG. 2 is a schematic cross-section view of one embodiment of a hearing device 100. The device 100 includes a housing 110 and hearing assistance components 120 disposed within the housing. Hearing assistance components 120 can include any suitable device or devices, e.g., integrated circuits, power sources, microphones, receivers, etc. For example, in one or more embodiments, the components 120 can include a controller 122 (e.g., controller 16 of FIG. 1), a microphone 124, a receiver 126 (e.g., speaker), a power source 128, an antenna 130, and one or more sensors 134, 136 (e.g., sensor 14 of FIG. 1). The microphone 124, receiver 126, power source 128, antenna 130, and sensors 134, 136 can be electrically connected to the controller 122 using any suitable technique or techniques.

Any suitable controller 122 can be utilized with the hearing device 100, e.g., the same controller or controllers described regarding controller 16 of system 10 of FIG. 1. For example, the controller 122 can be adapted to employ programmable gains to adjust the hearing device output to a patient's particular hearing impairment. The controller 122 can be a digital signal processor (DSP), microprocessor, microcontroller, other digital logic, or combinations thereof.

The processing can be done by a single processor, or can be distributed over different devices. The processing of signals referenced in this disclosure can be performed using the controller 122 or over different devices.

In one or more embodiments, the controller 122 is adapted to perform instructions stored in one or more memories 132. Various types of memory can be used, including volatile and nonvolatile forms of memory. In one or more embodiments, the controller 122 or other processing devices execute instructions to perform a number of signal processing tasks. Such embodiments can include analog components in communication with the controller 122 to perform signal processing tasks, such as sound reception by the microphone 124, or playing of sound using the receiver 126.

In general, digital hearing devices include a controller or processor. In such devices, programmable gains may be employed to adjust the hearing device output to a user's particular hearing impairment. The controller 122 (and controller 16 of FIG. 1) may be a digital signal processor (DSP), microprocessor, microcontroller, other digital logic, or combinations thereof. The processing may be performed by a single processor, or may be distributed over different devices. The processing of signals referenced in this application can be performed using the processor or other different devices. Processing may be done in the digital domain, the analog domain, or combinations thereof. Processing may be done using subband processing techniques. Processing may be done using frequency domain or time domain approaches. Some processing may involve both frequency and time domain aspects. For brevity, in some examples drawings may omit certain blocks that perform frequency synthesis, frequency analysis, analog-to-digital conversion, digital-to-analog conversion, amplification, buffering, and certain types of filtering and processing. In various embodiments, the processor is adapted to perform instructions stored in one or more memories, which may or may not be explicitly shown. Various types of memory may be used, including volatile and nonvolatile forms of memory. In various embodiments, the processor or other processing devices execute instructions to perform a number of signal processing tasks. Such embodiments may include analog components in communication with the processor to perform signal processing tasks, such as sound reception by a microphone, or playing of sound using a receiver (i.e., in applications where such transducers are used). In various embodiments, different realizations of the block diagrams, circuits, and processes set forth herein can be created by one of skill in the art without departing from the scope of the present subject matter.

The hearing assistance components 120 can also include the microphone 124 that is electrically connected to the controller 122. Although one microphone 124 is depicted, the components 120 can include any suitable number of microphones. Further, the microphone 124 can be disposed in any suitable location within the housing 110. For example, in one or more embodiments, a port or opening can be formed in the housing 110, and the microphone 124 can be disposed adjacent the port to receive audio information from the user's environment.

Any suitable microphone 124 can be utilized. In one or more embodiments, the microphone 124 can be selected to detect one or more audio signals and convert such signals to an electrical signal that is provided to the controller 122. Although not shown, the controller 122 can include an analog-to-digital convertor that converts the electrical signal from the microphone 124 to a digital signal.

Electrically connected to the controller 122 is the receiver 126. Any suitable receiver can be utilized. In one or more embodiments, the receiver 126 can be adapted to convert an electrical signal from the controller 122 to an acoustic output or sound that can be transmitted from the housing 110 to the user. In one or more embodiments, the receiver 126 can be disposed adjacent an opening 112 disposed in a first end 114 of the housing 110. As used herein, the term "adjacent the opening" means that the receiver 126 is disposed closer to the opening 112 in the first end 114 than to a second end 116 of the housing 110.

The power source 128 is electrically connected to the controller 122 and is adapted to provide electrical energy to the controller and one or more of the other hearing assistance components 120. The power source 128 can include any suitable power source or power sources, e.g., a battery. In one or more embodiments, the power source 128 can include a rechargeable battery. In one or more embodiments, the components 120 can include two or more power sources 128.

The components 120 can also include the optional antenna 130. Any suitable antenna or combination of antennas can be utilized. In one or more embodiments, the antenna 130 can include one or more antennas having any suitable configuration. For example, antenna configurations can vary and can be included within the housing 110 or be external to the housing. Further, the antenna 130 can be compatible with any suitable protocol or combination of protocols. In one or more embodiments, the components 120 can also include a transmitter that transmits electromagnetic signals and a radio-frequency receiver that receives electromagnetic signals using any suitable protocol or combination of protocols.

For example, in one or more embodiments, the hearing device 100 can be operatively connected to one or more external accessories or devices 102 (e.g., accessory 18 of FIG. 1) using, e.g., Bluetooth, Wi-Fi, magnetic induction, etc. For example, in one or more embodiments, the hearing device 100 can be wirelessly connected to the Internet using any suitable technique or techniques. Such connection can enable the hearing device 100 to access any suitable databases, including medical records databases, cloud computing databases, location services, etc. In one or more embodiments, the hearing device 100 can be wirelessly connected utilizing the Internet of Things (IoT) such that the hearing device can communicate with, e.g., hazard beacons, one or more cameras disposed in proximity to the user, motion sensors, room lights, etc. Further, in one or more embodiments, the hearing device 100 can access weather information via the Internet using any suitable technique or techniques such that the user can be informed of potentially hazardous weather conditions.

In one or more embodiments, the hearing device 100 can include the first sensor 134 and the second sensor 136. Although depicted as including two sensors 134, 136, the hearing device 100 can include any suitable number of sensors, e.g., 1, 2, 3, 4, 5, or more sensors. The sensors 134, 136 can include any suitable sensor or sensors, e.g., the same sensors described herein regarding sensor 14 of system 10 of FIG. 1. The first sensor 134 can include the same sensor as the second sensor 136. In one or more embodiments, the first sensor 134 includes a sensor that is different from that of the second sensor 136. The sensors 134, 136 can be operatively connected to the controller 122 using any suitable technique or techniques. Although depicted as being disposed within the housing 110 of the hearing device 100, one or both of the sensors 134, 136 can be disposed in any suitable location relative to the hearing device. Further, in one or more embodiments, one or both of the sensors 134, 136 can be associated with the accessory 102, e.g., disposed within the accessory, operatively connected to the accessory, etc.

In one or more embodiments, first sensor 134 is operatively connected to the hearing device 100 and adapted to detect a first characteristic of the user and generate a sensor signal based on the first characteristic. In one or more embodiments, the second sensor 136 is operatively connected to the hearing device 100 and adapted to detect a second characteristic of the user and generate a second sensor signal based on the second characteristic. The first and second characteristic of the user can be any suitable characteristic, e.g., at least one of a physiological characteristic and an environmental characteristic of the user. The controller 122 can be adapted to determine a fall risk value based on the sensor signal from the first sensor 134 and the second sensor signal from the second sensor 136. The first and second characteristics can include any suitable characteristic, e.g., the same characteristic or characteristics described herein regarding sensor 14 of system 10 of FIG. 1. The characteristic detected by the first sensor 134 can be the same as or different from the second characteristic detected by the second sensor 136. For example, in one or more embodiments, the characteristic detected by the first sensor 134 can be eye movement of the user and the second characteristic detected by the second sensor 136 can be head movement of the user. In such embodiments, the controller 122 can be adapted to determine the fall risk threshold by measuring a maximum displacement between a longitudinal axis of the user and a normal to the earth's surface as a function of time based on the second sensor signal 136. In one or more embodiments, the controller 122 can be adapted to determine the fall risk threshold by measuring a maximum velocity of displacement between a longitudinal axis of the user and a normal to the earth's surface based on the second sensor signal.

Returning to FIG. 1, the sensor 14 is operatively coupled to the hearing device 12. The sensor 14 can be operatively coupled to the device 12 using any suitable technique or techniques, e.g., electrical, optical, or wireless coupling. The sensor 14 can be disposed in any suitable location. In one or more embodiments, the sensor 14 can be a component of hearing assistance components of the hearing device 12, e.g., such as sensors 134, 136 of hearing assistance components 120 of FIG. 2. In one or more embodiments, one or more sensors 14 can be disposed outside of the housing of the hearing device 12 and operatively coupled to the device and the controller 16 using any suitable technique or techniques. In one or more embodiments, one or more sensors can be associated with or a component of the accessory 18. In one or more embodiments, one or more sensors 14 can be disposed within one or both ears and outside the ear of the user.

The sensor 14 can include any suitable sensor or sensors. For example, the sensor 14 can include at least one of an accelerometer, barometer, gyroscope, heart rate sensor, blood pressure sensor, magnetometer, eye sensor, EEG sensor, blood sugar sensor, light sensor, sweat sensor, pupillometry sensor, cerumen sensor, cortisol sensor, body temperature sensor, humidity sensors, air quality sensor and combinations thereof. The sensor 14 can be adapted to detect any suitable characteristic of the user, e.g., at least one of a physiological characteristic and an environmental characteristic of the user. For example, the physiological characteristic can include at least one of body position, eye movement, body temperature, heart rate, EEG, skin impedance, and combinations thereof.

Further, in one or more embodiments, the sensor 14 can be adapted to detect one or more environmental or ambient characteristics proximate to the user of the hearing device 12. For example, such sensor 14 can include at least one of an ambient temperature sensor, barometer, microphone, GPS sensor, moisture/humidity sensor, image sensor (i.e., a camera), and combinations thereof. The sensor 14 can be adapted to detect any suitable environmental characteristic or characteristics, e.g., temperature, moisture/humidity, sound, light intensity, terrain, elevation, ambient oxygen levels, pollutants, toxins, carbon monoxide levels, and combinations thereof.

Operatively connected to the hearing device 12 is the accessory 18. In one or more embodiments, the accessory 18 can also be operatively connected to one or both of the controller 16 and the sensor 14. In one or more embodiments, the accessory 18 is adapted to be worn on the body of the user of the hearing device 12, i.e., a body-worn accessory. In one or more embodiments, the accessory 18 is adapted to be disposed apart from the body of the user of the hearing device 12, i.e., an off-body accessory.

In general, data from the accessory 18 (i.e., accessory data) can be utilized to assist in determining one or both of a fall risk value and a fall risk threshold of the user using any suitable technique or techniques. In one or more embodiments, the accessory 18 along with the sensor 14 can provide an ecosystem that can enhance the overall performance of the fall prediction system (e.g., sensitivity, specificity) through signal redundancy with signals provided by the sensor 14. In one or more embodiments, one or more signals from the accessory 18 can be compared with one or more signals from the sensor 14 to determine the accuracy of data being collected by the sensor.

The accessory 18 can include any suitable accessory or accessories. For example, the accessory 18 can include at least one of a TV streamer, wireless audio streaming device, cell phone or landline streamer, remote control, Direct Audio Input (DAI) gateway, audio gateway, microphone, telecoil receiver, hearing device programmer, charger, drying box, smartwatch, smartphone, smart glasses, a captioning device, a wearable or implantable health monitor, and combinations thereof.

In one or more embodiments, such accessories can include a microphone input for "listening" for alarms. Alarms such as fire, burglar, CO, etc., and alerts such as a doorbell, weather alert, etc., can be activated when a hearing aid user is using the hearing device or when the user is in the process of listening to digital audio inputs from accessory devices that will further impair the user from hearing these household alarms or alerts. In addition, a user would be less likely to hear an incoming telephone call or doorbell when steaming audio via an accessory device. In one or more embodiments, the wireless accessories or dedicated accessory or audio gateway type devices can be equipped with a microphone. The microphone is used as an input to monitor the ambient acoustic environment to determine if an alarm is sounding. The unit can be put in a training mode before being deployed for use to "learn" the alarm sounds so that each can be distinguished and then unique alerts can be sent to the hearing aid user for each alarm, or a generic alert can be sent just to alert the user that an alarm is sounding or a phone is ringing. In one or more embodiments, acoustic inputs can be wirelessly forwarded to hearing instruments from accessory devices. Accessory devices may include cell phones or smartphones having wireless communication capability such as 802.11 (WIFI), Bluetooth, or other means of wireless communication with a hearing instrument.

The accessory 18 can be operatively connected to the hearing device 12 using any suitable technique or techniques. In one or more embodiments, the accessory 18 can be connected to the hearing device 12 by a wire. In one or more embodiments, the accessory 18 can be connected to the hearing device 12 using any suitable wireless technology, e.g., Bluetooth Classic, Bluetooth Low-Energy, 900 MHz, 2.4 GHz, ISM frequencies, NFMI, FM, Wi-Fi, LTE, and combinations thereof. Any suitable technique or techniques can be utilized to operatively connect the accessory 18 to the hearing device 12, e.g., one or more of the techniques described in U.S. Pat. No. 8,169,938, entitled COMMUNICATION SYSTEM FOR WIRELESS AUDIO DEVICES.

Any suitable data or information can be communicated between the accessory 18 and the hearing device 12, controller 16, and/or sensor 14. In one or more embodiments, such data can include streaming audio data, software or program data, variable or parameter data; biometric data; environmental data; control signals, security or encryption data; diagnostic data; and/or status data.

The accessory 18 can also include one or more sensors that are adapted to provide a sensor signal representative of a characteristic of the user or of the environment proximate to the user (i.e., an environmental characteristic of the user). In one or more embodiments, the accessory 18 can include the first sensor (e.g., sensor 134) or the second sensor (e.g., sensor 136) such that one or more of the sensors is associated with the accessory, and the one or more sensors are adapted to detect a characteristic of the user or of the environment proximate to the user, and generate a sensor signal based on the characteristic. In one or more embodiments, the one or more sensors may be distributed between both the hearing device and the accessory. For example, the first sensor 134 may be disposed in the accessory 18 and the second sensor 136 may be disposed in the hearing device 12.

In one or more embodiments, the accessory 18 can be utilized for exergames for the user such as described, e.g., in U.S. patent application Ser. No. 15/589,298, filed May 8, 2017, and entitled HEARING ASSISTANCE DEVICE INCORPORATING VIRTUAL AUDIO INTERFACE FOR THERAPY GUIDANCE. Exergames (a.k.a. "fitness games") are a form of physical therapy/fitness training that is delivered through use of an entertainment medium, typically video games.

Exergaming relies on technology that tracks body movement or reaction. These technologies can include body-worn sensors (e.g., accelerometer/gyroscope) or other sensors that monitor the user from some distance (e.g., a camera). The Xbox Kinect and the Wii Fit Board are most often used in exergaming, but there has been a recent push for the use of body-worn sensors.

The basic premise of exergaming is to encourage and motivate users to perform and practice physical activities. The paradigm leverages gamification, coaching, and the ability of others to remotely monitor the user. Leading a sedentary lifestyle can cause to lower limb muscle weakness, reduced endurance, and ultimately an increased risk for falling. Research indicates that exergames training programs can produce measurable improvements in fitness, improve balance ability, reduce the cognitive load required to navigate obstacles when walking (this is especially relevant to patients with Parkinson's Disease), and reduce falls risk.

In one or more embodiments, the accessory 18 (e.g., TV audio streamer) can be utilized to administer exergaming in such a way that the user's movements during the exergaming can be used to aid in determining a fall risk of the user of the system 10. In one or more embodiments, a combination of body-worn and off-body sensors may be used. For example, a body-worn sensor may be disposed in a hearing device 12 or accessory 18 which is worn by the user (e.g., remote control) while an off-body sensor may be associated with an off-body accessory 18 (e.g., TV streamer). Information provided by such sensors can either be in the form of results/trends of scored activities (i.e., cumulative scores, levels reached, time spent playing, etc.) or from the raw motion data observed during the games themselves (e.g., postural stability, limits of stability, reaction speed, etc.).

In addition to providing treatment routines, the system 10 including the accessory 18 can also be used to administer falls risk screening measures. These screening measures could either be embedded into game form (i.e., gamified) or more directly through specific directions provided to the user.

One example of a screening measure would be to ask the user to stand on one leg and monitor the stability of the user during the activity. Another example would be to measure the user's reaction speed to an event. In the case of the TV streaming accessory 18, visual guidance and feedback can be displayed by the television, and the audio could be displayed either by the entertainment system's speakers or by using the hearing device via the accessory's operative connection to the hearing device 12. In one or more embodiments, the use of both visual and hearing stimuli would allow for assessment of the user's cognitive abilities during physical activities, i.e., a "dual-task paradigm." In another example, lifelike walking scenarios may be presented with obstacles or distractions that the user will either need to navigate around or ignore.

To facilitate the exergames activities, the accessory 18 may either contain or be operatively connected to any appropriate sensors or additional devices for monitoring the user's movements and reactions. For example, a TV streamer accessory 18 can either contain a camera or be operatively connected to a camera. Similarly, the TV streamer accessory 18 can be operatively connected to a balance board or force plate such as the Wii Fit Board or dance mats. Sensors housed inside the hearing device 12 and the accessory 18 could also be used to record the motions and reactions of the user. For example, one embodiment of an exergame may be administered using a treadmill that perturbates the user's gait, and the reactive motions are recorded by at least one of the hearing device 12, controller 16, and accessory 18.

In one embodiment, a visual display accessory 18 may be virtual reality goggles that are operatively connected to at least one of the hearing device 12 and the controller 16. Similarly, smart glasses or contact lenses may be used to present a visually augmented reality space.

The accessory 18 can also connect to the internet and store data in the cloud. This can allow peers to compete and interact with each other and permit healthcare providers and caregivers to monitor progress of the user.

The accessory 18 can be utilized in any suitable setting. In one or more embodiments, the accessory 18 can be utilized at home. Further, in one or more embodiments, the accessory 18 can be utilized in a clinic.

Operatively connected to the hearing device 12 is the controller 16. In one or more embodiments, the controller 16 can also be operatively connected to one or both of the sensor 14 and the accessory 18. The controller 16 can include any suitable controller or controllers, e.g., the same controller described regarding controller 122 of the hearing device 100 of FIG. 2. The controller 16 can be disposed in any suitable location relative to the hearing device 10, the sensor 14, and the accessory 18. In one or more embodiments, the controller 16 is disposed within the housing of the hearing device 12, e.g., within housing 110 of hearing device 100 of FIG. 2. In one or more embodiments, the controller 16 can be disposed external to the hearing device 12 such that it is associated with the accessory 18, e.g., disposed within the accessory, operatively connected to the accessory, etc. In one or more embodiments, the controller 16 can include a first controller disposed within the hearing device 12 and a second or additional controllers disposed externally to the hearing device, e.g., associated with the accessory 18.

Figure 3:
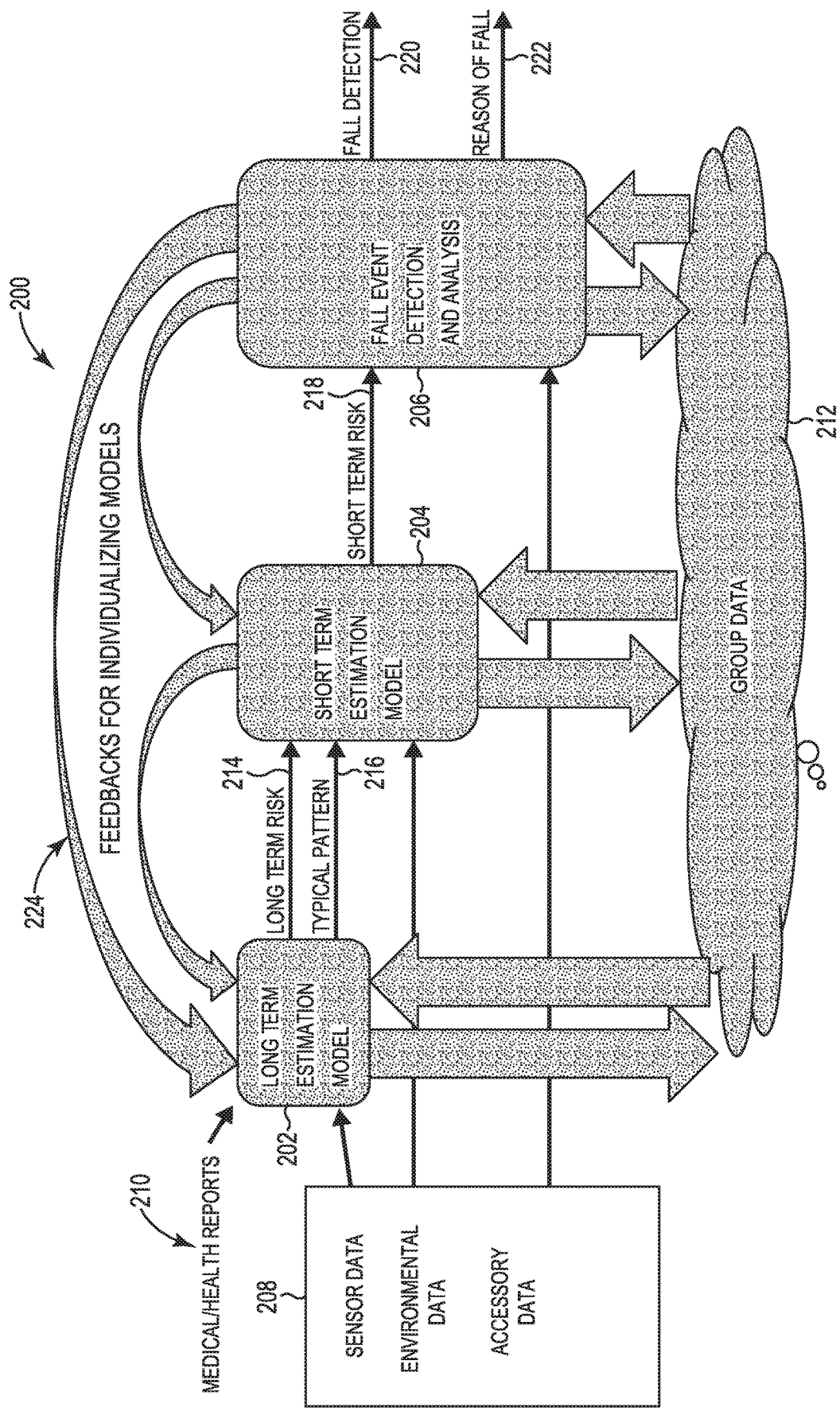
FIG. 3 is a flow chart of one embodiment of a method of utilizing the fall prediction system of FIG. 1.

The controller 16 can be adapted to perform any suitable function or functions to process inputs from any suitable source or sources and provide an estimation of the risk of a fall. In one or more embodiments, the controller 16 can be adapted to detect falls. For example, FIG. 3 is a flow chart of one embodiment of a method 200 of predicting and detecting a fall event. Although described in regard to the fall prediction system 10 of FIG. 1, the method 200 can be utilized with any suitable system or device. In one or more embodiments, the method 200 includes generating a long-term fall estimation model 202, generating a short-term fall estimation model 204, and detecting a fall event 206.

For generating one or more of the long-term fall estimation model 202, the short-term fall estimation model 204, and the fall event detection 206, a risk or probability value of a fall can be based on a predetermined formula or formulas that can be derived from experimental data. The formula can also be entirely learned or modified through various machine learning approaches. For example, when a fall event is detected at 206, the method 200 can send data collected before the event by one or more sensors 14, e.g., to a cloud server 212. In one or more embodiments, data from the user and other users can be used to train a regression model or deep neural network to estimate the risk of a fall for an individual user.

At each stage 202, 204, 206, different actions can be taken or outputs provided to aid in preventing a fall or reducing the severity of a fall. For example, when a long-term risk value 214 generated by the long-term fall estimation model 202 is determined to exceed a fall risk threshold, the system 10 can generate a fall prevention output that includes notifying one or more of the user, caregiver, and medical professional for proper diagnosis and treatment. The fall risk threshold can be based upon any suitable data from one or more sensors 14 of the system 10, e.g., one or more settings of the accessory 18. When a short-term fall risk value 218 generated by the short-term estimation model 204 exceeds a fall risk threshold, the system 10 can generate a fall prevention output that includes sending a warning signal to the user, increasing an intensity of the ambient light for the user's environment, notifying other IoT devices proximate to the user to help prevent the fall or otherwise protect the user from injury, etc. If a fall event is detected at 206, the system 10 can monitor the user's physiological characteristics, notify a caregiver, notify a medical professional, etc.

The long-term fall estimation model 202 can be generated from analytics or machine learning of larger group data using any suitable technique or techniques, e.g., regression, steady-state, Bayesian, classification trees, Volterra, support vector machine, Gaussian mixture, neural network techniques, and combinations thereof.

The long-term estimation model 202 can provide an estimate or probability of the general risk (or capability of keeping balance) of the user and learn the user's norms regarding motion patterns and health/physiological information. Inputs for generating the long-term fall estimation model 202 can either be obtained based on clinical evaluations and medical history, or be learned by the fall prediction system 10 from inputs provided by various types of sensors, e.g., sensor 14. For example, motion patterns of the user and changes to such patterns can be estimated and monitored based on the outputs from one or more of an inertial measurement unit (IMU) sensor, GPS sensor, barometer, magnetometer, EEG sensor, camera, etc. The motion of the user may include sway amplitude and speed while walking, speed and trajectory when sitting down or standing up, speed and radius when turning, stride length, symmetry and variance, reaction speed, etc. In one or more embodiments, physiological characteristics that can be provided as inputs to the long-term estimation model 202 include heart rate, blood pressure, blood sugar, blood oxygen, core body temperature, etc., and can be monitored utilizing any suitable sensor or sensors 14. All such inputs and how they change over time can be monitored and used to estimate the long-term fall risk 214 (i.e., how prone the user is to a fall).

Any suitable inputs can be utilized to generate the long-term fall estimation model 202. For example, in one or more embodiments, data inputs 208 such as sensor and accessory data from one or more sensors (e.g., sensor 14) and one or more accessories (e.g., accessory 18) related to physiological characteristics of the user, environmental data regarding the environment proximate to the user (i.e., an environmental characteristic of the user), and combinations of physiological and environmental characteristics or data can be utilized by the long-term estimation model 202 to determine the fall risk value 214. Medical/health reports 210 regarding the user can also be provided as inputs to the long-term fall estimation model 202. Further, group data from the cloud 212 can also be provided as inputs to the long-term fall estimation model 202.

The method 200 further includes generating the short-term fall estimation model 204. In one or more embodiments, the model 204 can generate a short-term fall risk value or probability. Such short-term fall risk value 218 can be based on any suitable input or inputs. For example, in one or more embodiments, this risk value 218 can be based on the detection of one or more signature indicators, such as abnormal eye movement, sudden drop of blood pressure or blood sugar, abnormal heart rate, sudden increase of sway speed and amplitude, a quick change in elevation, ambient temperatures near freezing, etc. The seriousness of the detected inputs can be derived by comparing such inputs to averaged norms of the user's age group and then, together with certain environmental data, used to estimate the short-term fall risk value 218.

Further, typical patterns of the user can be provided as inputs 216 to the short-term fall estimation model 204. Such typical patterns 216 can be determined based upon various parameters, including gait, postural transitions, and general activity levels of the user. For example, the user's typical patterns 216 can be determined based upon, e.g., walking speed, cadence, gait symmetry and variance, step clearance, sway, speed of postural transitioning (how long it takes to stand up or sit down), total number of steps per day, number of transitions each day, number of walks per day, distance or duration of each walk on average, total walking distance per day, etc.

In one or more embodiments, the averaged group norms can be replaced by the values that are adjusted based on the user's normal behaviors that are learned when generating the long-term fall estimation model 202. The user's long-term fall risk value 214 can also be an input for the short-term fall estimation model 204 when generating the short-term fall risk value.

Various sensors 14 (e.g. IMU, barometer) or accessories 18 can be used to detect a fall 220 at 206. The short-term and long-term fall risk values 214, 218 can also be incorporated to increase a confidence interval of the fall detection 206 and reduce false positives. In addition, physiological data collected before the fall event 220 can be used to help analyze a reason or reasons for the fall 222. Any suitable technique or techniques can be utilized to store, transmit, and analyze the physiological data once a fall event or near fall event has been detected.

In one or more embodiments, the method 200 can include one or more feedback pathways 224 for individualizing one or more of the long-term fall estimation model 202 and the short-term fall estimation models 204.

Returning to FIG. 1, the fall prediction system 10 can be utilized to receive input information and determine the likelihood or probability that the user of the fall prediction system will fall. In one or more embodiments, the fall prediction system 10 can be utilized to receive input information from any suitable source to determine whether the user has fallen. The input information can be provided using any suitable sensor or accessory. For example, the input information can be provided to the controller 16 by the sensor 14, the hearing device 12, the accessory 18, manually by one or more of the user, a caregiver, and a medical professional, or obtained from other systems via wired or wireless connections to system 10.

Further, the fall prediction system 10 can provide any suitable outputs that can be based on the probability of a fall or that a fall has occurred. Any suitable output or outputs can be provided by the system 10, e.g., notifications, reports, IoT triggers (e.g., activating room lighting), treatments to the user of the device 12, etc. In one or more embodiments, the system 10 can be utilized to detect head or body impact, check with the user for consciousness, and inform one or more of the user, caregiver, and medical professional of the detection of a head or body impact and level of consciousness of the user.

The fall prediction system 10 can utilize any suitable technique or techniques to determine the risk of a fall and/or that a fall has occurred. For example, in one or more embodiments, the controller 16 can be adapted to determine a fall risk value based on one or more inputs. The fall risk value can be any suitable value or scale that correlates to a probability that the user may experience a fall.

Further, any suitable technique or techniques can be utilized to determine the fall risk value. For example, the controller 16 can be adapted to determine the fall risk value based on a sensor signal generated by one or both of the sensor 14 and the accessory. The sensor signal can be based on one or more physiological and/or environmental characteristics detected by the sensor 14 or accessory 18. The controller 16 can be further adapted to determine the fall risk value based on other inputs as well. For example, in one or more embodiments, one or more inputs can be provided by one or more of the user, the caregiver, and the physician. For example, one or more inputs can be provided by the user in response to one or more queries provided, e.g., by the hearing device 12, the accessory 18, the caregiver, or the physician.

In one or more embodiments, postural transition or sway (i.e., displacement of the head of the user in three dimensions) of the user can be monitored to determine a fall risk value. Any suitable sensor or sensors 14 can be utilized to determine postural sway or stability, e.g., one or more of an accelerometer, gyroscope, microphone, barometer, optical sensor, and bioelectrical sensor. In one or more embodiments, the sensor 14 can include an accelerometer and a gyroscope as the primary sensors for postural balance and fall-risk monitoring and the other sensors can be secondary sensors. For example, a secondary sensor can include a microphone that may be used for detecting footfalls or a fall event. Further, a barometer may be used to detect stair climbing or a fall event. In addition, an optical sensor may be used for measuring heart rate and other biosignals. A bioelectric sensor may be used for monitoring electro-, cardio-, encephalo-, occulo-, and myo-graph signals from any location on the head and body of the user.

In general, there can be multiple activities and postures during which one may fall down, most commonly walking and standing, transitions between postures such as movement between standing and sitting, etc. Further, there can be identifiable physiological events that precede the fall, such as postural hypotension.

One or more physiological sensors 14 may be employed to identify a "prodrome" of a postural instability. Some possible techniques of using this sensor information for this purpose can be used individually or in combination.

For example, in one or more embodiments, the sensor 14 can include one or more of an accelerometer, a gyroscope, a magnetometer, and a camera. Further, the sensor 14 can be disposed in the hearing device, the accessory 18, or operatively connected to one or both of the hearing device and the accessory. Signals form the sensor 14 can be used to compute and monitor a deviation from a stable position and a velocity with which that takes place. In one or more embodiments, the controller 16 can utilize the signal inputs from the sensor 14 to generate a measure of postural stability. Postural stability can be recorded during normal daily activities, including standing, walking, postural transitions, and climbing stairs. In some embodiments, postural stability can be recorded during structured activities such as exergames. A threshold of normal stability can be established based on clinical postural stability testing, during typical activities of daily living, or during a user initiated initialization involving one or more of these activities. Measurements in case of a recorded fall can be used to adjust the threshold, if appropriate.

Acceleration of the head of the user while walking is complex, with the most prominent feature in the unprocessed accelerometer signal being that of the footfall. Adding to this complexity can be stabilization of the head by the neck. Footfall signals may be diminished by neck stabilization but still can be detectable. Vestibular-ocular reflexes can also be measured as the eye will attempt to stabilize the individual's visual field with each step. In one or more embodiments, head oscillation in three dimensions (anteroposterior (AP), lateral, and vertical) can measured. Components of the displacement and the velocity in each dimension can be computed as measures of the postural stability. Although generally correlated and constrained by the body, the head can move relatively independently, which introduces artifacts. To mitigate these artifacts, in one or more embodiments, the velocity and displacement of the head oscillation are computed only when the pitch, yaw and/or roll motions of the head a slower than some predefined thresholds. Artifacts related to head movements may also be mitigated, by the controller, through the integration of sensor inputs of body-worn sensors placed on the chest, trunk, waist, etc. The values can depend upon the speed and type of body movement.

In one or more embodiments, the controller 16 can be adapted to determine the fall risk threshold by measuring a maximum displacement between a longitudinal axis of the user and a normal to the earth's surface as a function of time. Further, in one or more embodiments, the controller 16 can be adapted to determine the fall risk threshold by measuring a maximum velocity of displacement between a longitudinal axis of the user and a normal to the earth's surface.

Thresholds of safe postural stability or limits of stability can be established by balance testing in a clinical setting or by user-conducted, self-directed tests. A fall risk signal or other fall risk output can be generated based on single or multiple threshold crossings.

Parameters of postural stability, i.e., balance metrics, and fall risk values or probabilities can be of interest to one or more of the user, caregivers such as the family members, and medical professionals. Balance metrics and fall risk values may be monitored daily and transmitted to various parties. Once a fall risk threshold is exceeded, a fall risk output such as a discrete audio alert may be provided to the user. In laboratory conditions, head worn IMU sensors can be utilized to characterize small motions (e.g., sway) that can be important for balance evaluation. The orientation of the IMU sensors, however, is highly controlled and well calibrated in the laboratory. In practice, when users are wearing two hearing devices, proper alignment of the IMU sensors at each side of the head is desired. Any suitable technique or techniques can be utilized to align the sensor 14 in both left and right hearing devices of the system 10, e.g., the techniques described in U.S. patent application Ser. No. 15/331, 230, filed Oct. 21, 2016, and entitled HEAD RELATED TRANSFER FUNCTION INDIVIDUALIZATION FOR HEARING DEVICE. In one or more embodiments, a technique can be utilized to compensate for the orientation mismatch between two hearing devices so that the IMU sensors on both sides of the head can be collaboratively aligned with the head orientation and used to derive postural stability information.

In one or more embodiments, the fall risk value based upon postural stability can be determined by first detecting that the user is walking. One or more artifacts from the sensor 14 caused by foot-impact can be filtered out using any suitable technique or techniques. Postural stability can be determined using any suitable technique or techniques. Velocity components of such postural stability can be determined using any suitable technique or techniques. In one or more embodiments, the fall risk value can be based upon walking speed, distance walked, frequency of walks, duration of walks, frequency of successful postural transitions, speed of postural transitions, or activity classifications, and combinations thereof.

A composite sensitivity parameter of the contribution of the sensor 14 (e.g., one or more accelerometers) to the overall fall risk value can be determined using any suitable technique or techniques. In one or more embodiments, the sensitivity of the fall risk value to an amplitude of the postural stability can be determined using, e.g., one or more of a user input after a near-fall event, a balance study, and fall detection. The sensitivity of the fall risk value to the stability velocity at a pre-determined postural stability can be determined using, e.g., one or more user inputs after a near-fall event, a balance study, and fall detection. Further, the sensitivity of the fall risk value to a statistically determined combination of the postural stability and the sway velocity can also be determined.

In one or more embodiments, postural stability, sway velocity and other posture, walking and fall-related information can be routinely transmitted to healthcare professionals. The user's posture while standing and walking, actual fall events, and user-indicated near-fall events can also be transmitted to healthcare professionals.

If the fall risk value exceeds the fall risk threshold, then an alert can be sent to one or more of the user, caregiver, and medical professional. Such alert can include instructions for how to prevent a fall from occurring.

In one or more embodiments, sensors 14 having one or more accelerometers can be placed in both ears of the user. Acceleration of the mid-point between the two ears, as opposed to that of one ear, can be calculated to determine postural stability. Further, false positives of fall detection can be reduced by ensuring both sensors 14 follow the same nominal motion pattern. In addition, head rotation around the vertical axis i.e., the yaw, can also be determined and utilized to calculate the fall risk value. In one or more embodiments, the sensors 14 if associated with the accessory 18 can also assist in reducing false positives. Further, body-worn accessories 18 can also assist in measuring body motion from the body's center of gravity.

In one or more embodiments, a short-term estimation model (e.g., model 204 of FIG. 3) can be determined by measuring eye movement of the user. For example, the fall prediction system 10 can detect eye movements and compare such eye movements to a baseline to determine whether a vestibular event is occurring that may increase the risk of fall. The sensor 14 of the fall prediction system 10 can include one or more eye movement sensors. In one or more embodiments, the system 10 can also include one or more sensors 14 that can measure head movement of the user. Data from such head movement sensors 14 can be utilized to correlate with eye movement sensor data to determine the risk of a fall. Any suitable fall prediction system or device can be utilized to measure eye movement of a user, e.g., the devices described in U.S. Pat. No. 9,167,356, issued Oct. 20, 2015, and entitled ELECTROOCULOGRAM AS A CONTROL IN A HEARING ASSISTANCE DEVICE.

Figure 4:
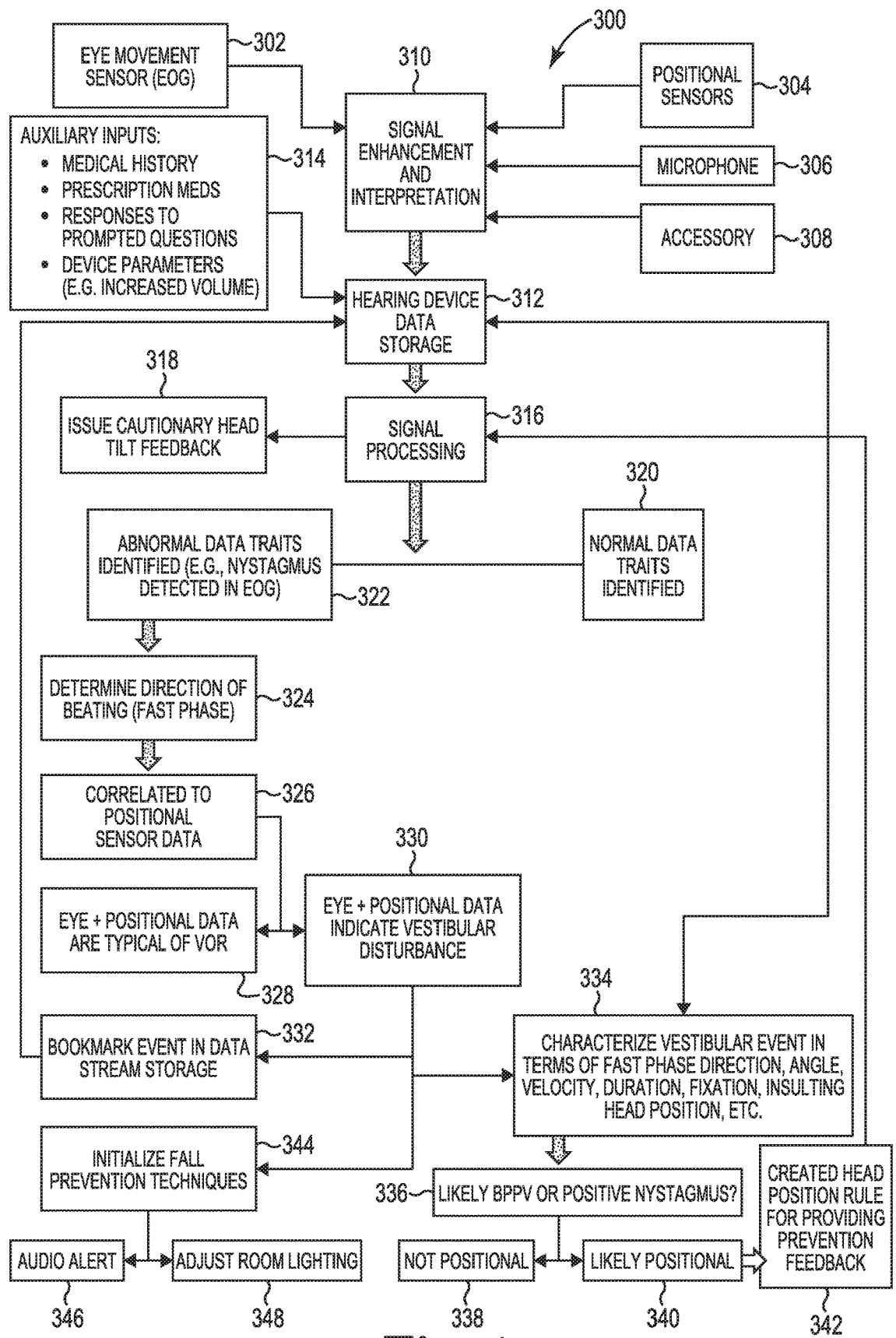
FIG. 4 is a flow chart of another embodiment of a method of utilizing the fall prediction system of FIG. 1.

FIG. 4 is a flow chart of one embodiment of a method 300 for predicting and detecting a fall that utilizes eye movement data. Although described in reference to fall prediction system 10 of FIG. 1, the method 300 can be utilized with any suitable system or systems. In one or more embodiments, data from eye movement sensors 302 (e.g., Electrooculography (EOG) sensors) and positional sensors 304 (collectively sensor 14 of FIG. 1) can be utilized for early detection of peripheral vestibular asymmetry (which generally cause nystagmus and feelings of imbalance/dizziness to occur). Nystagmus is an involuntary oscillation of one or both eyes about one or more axes. The eye movement sensors 302 can allow the system 10 to make one or more of the following determinations: (a) whether or not the nystagmus is typical given the user's baseline movement data, (b) whether the user's visual pursuits are smooth or otherwise atypical. Other sensors can be utilized with the method 300 to predict and/or detect falls. For example, the system 10 can include at least one of a microphone 306 and a sensor 308 associated with an accessory (e.g., accessory 18).

In one or more embodiments, the controller 16 can also be adapted to determine the fall risk threshold by first calculating one or more of the direction of visual gaze, the direction of body movement, and the ambient light level, and then inferring the likelihood that the movements of the user are adequately coordinated with visual sensory input. For example, an individual is at higher risk for falling when moving backwards, towards a chair, when attempting to sit down, etc. Similarly, an individual is at a greater risk for falling when looking away from their walking path or when the walking path is not well-illuminated. Once a fall risk threshold is exceeded, a fall risk output such as a discrete audio alert may be provided to the user, and the ambient light level may be increased for the user. Parallel positional sensors (as in the case of a binaural set of equipped hearing devices or systems or accessories) can also be used to detect falls. The use of two separate, but parallel, positional sensors can provide redundancies that can prevent false fall detections (e.g., if the user removes or drops the fall prediction systems, the data from the system's axis sensors will not indicate synchronous movements in the same way that they would if being worn during a fall event). Further, one or more sensors associated with the accessory can be utilized to assist in confirming whether a fall has occurred.

One or more signals from the sensors 302, 304, 306, 308 can be enhanced and interpreted using any suitable technique or techniques at 310. The enhanced signals can be stored using any suitable data storage device at 312. Further, auxiliary inputs 314 such as medical history, prescription medication records, responses to prompted questions by the user, and any device parameters such as increased sound volume level of the device can also be stored at 312. For example, manual increases in the volume level of the hearing device 12 enacted by the user may indicate that a shift in hearing sensitivity of the user may have occurred. Such changes in hearing sensitivity may be clinical indications of Meniere's disease or endolymphatic hydrops.

At 316, any suitable technique or techniques can be utilized to process the signals from the various devices and interpret the auxiliary inputs. In one or more embodiments, the sensor signals are filtered and noise in the signal is rejected. Data from the eye movement sensor 302 and the positional sensors 304 can be analyzed to determine the direction of simultaneous head and eye movements (i.e., determine gaze). A warning based upon this data can be provided to the user or caregiver at 318 if such data indicates an imminent fall.

The processed signals can be analyzed to determine normal data traits at 320 using any suitable technique or techniques. Such normal data traits can indicate smooth eye and head movements. Further, at 322, abnormal data traits such as nystagmus can be identified using any suitable technique or techniques. Such abnormal data traits can include abnormal signatures of head and eye movements. Further, nystagmus can be observed in eye movement sensor data. Nystagmus can be identifiable when the user's eyes exhibit both a fast movement phase followed by a slow movement phase in the opposite direction of the fast phase. Nystagmus can appear as a pattern of repeated fast phase and slow phase eye movements. Further, the abnormal signatures may include abnormal head movement, which may include rapid movement, detection of free fall or impact, etc.

At 324, the direction of beating (fast phase) of the user's eye movements can be determined using any suitable technique or techniques. The eyes can be determined to be beating in one direction (e.g., right or left), in alternating directions (i.e., right and left), or torsional (i.e., in a twisting motion to right or left and either up or down).

The data regarding the direction of beating of the eyes can be correlated to positional sensor data at 326 using any suitable technique or techniques. For example, eye motion data can be analyzed within the context of the measured head movement (i.e., positional data).

At 328, eye movement and positional data indicate that a typical vestibulo-ocular Reflex (VOR). In other words, eye movement and positional data indicate that the user's eyes move in opposite angular directions of the head when the user is maintaining a steady gaze. In one or more embodiments, the eye movement and positional data indicate typical optokinetic responses, i.e., nystagmus is present when the user experiences a rapid velocity (e.g., when looking through the window of a car and watching the trees pass by).

At 330, eye movement and positional data indicate that the user is experiencing a vestibular disturbance. Such disturbance can be determined when nystagmus is present when the head is not moving, when the eyes are moving in alternating directions, when the onset of nystagmus follows seconds after a movement of the head (usually—but not always—when the head is tilted upward), or when such nystagmus persists for greater than several seconds.

The event can be bookmarked in data storage at 332 using any suitable technique or techniques. For example, a rolling buffer of data can be kept, and when an event is detected in the data stream, that segment can be recorded and tagged for manual interpretation later. This can include a time window before conditions were observed, which may show data regarding the possible cause of the balance event. This data can be shared with medical professionals such as physicians, audiologists, and physical therapists to assist in a rapid differential diagnosis of the user.

At 334, the vestibular event can be characterized in terms of, e.g., fast phase direction, angle, velocity, duration, fixation, insulting head position, etc., using any suitable technique or techniques. For example, the detected event can be classified based upon relevant parameters of the detected head and eye movements.

At 336, a determination can be made as to whether a likely Benign Paroxismal Positional Vertigo (BPPV) or positional nystagmus has occurred using any suitable technique or techniques. For example, a determination based upon the classification of parameters can be made to determine whether BPPV or positional nystagmus has occurred.

At 338 a determination is made that the event is not positional in nature. For example, the event is considered to be non-positional if the nystagmus does not occur within about 30 seconds after a head/posture change (i.e., crosses a given threshold to make these determinations).

The event can be determined to be likely positional in nature at 340 using any suitable technique or techniques. For example, the event could be related to BPPV if the nystagmus of the user initiates within about 30 seconds after a head/posture change (crosses a given threshold to make these determinations), the nystagmus lasts for less than 60 seconds, and the nystagmus fatigues (i.e., is weakened or absent) if the provoking head position occurs again within a short time frame (minutes). In another example, the event could be related to positional cervicogenic dizziness if the nystagmus of the user initiates within about 30 seconds after a head/posture change (crosses a given threshold to make these determinations), the nystagmus lasts minutes to hours; additionally, the user or medical history of the user may indicate neck pain or injury (e.g., whiplash), headache or lightheadedness, or head-worn sensors may indicate decreases in blood pressure or oxygenation. Further, for example, the event is likely positional in nature if the nystagmus reverses or ceases when the user returns to the pre-provocation position.

At 342, if the event is determined to be related to the position of the user, then a head position rule can be created for providing prevention feedback to the user. For example, if positional nystagmus, cervicogenic dizziness or BPPV are suspected, then the provoking head position/maneuver are identified and stored. A cautionary head tilt feedback warning can be provided to the user when the user's head is in the undesired position. Further, feedback can be provided to the user if the user's head moves into the undesired position.

Upon the detection of an abnormal nystagmus disturbance, the system 10 can perform one or more of the following tasks: (a) alert the user to prepare for a spell of dizziness (e.g., instruct the user to sit down or brace himself so that the user does not fall) at 344; (b) alert a caregiver or medical professional via a connected messaging device at 346; (c) log the data from the event to determine the length, regularity, and severity of the disturbance; and (d) adjust the lighting within the environment of the user so as to assist the user in navigating and visually fixating so as to prevent a future fall at 348. Any suitable technique or techniques can be utilized to terminate such feedback that is provided to the user. For example, if a medical professional or virtual therapy guidance system (as described, e.g., in U.S. patent application Ser. No. 15/589,298) corrects the positionally provoked condition, then the user may not need to continue being discouraged from entering that position (until the next observed instance that may or may not occur again).

Correlated data from one or both hearing devices 12 and the accessory 18 can be used in assisting the medical diagnosis. For example, short episodes (e.g., 1-2 minutes in duration) that occur following a head tilt can be identified as BPPV. Knowing the direction of head tilt that provokes dizziness (and the subsequent direction of nystagmus beats) would offer even greater diagnostic specificity.

For example, the direction of head tilt and nystagmus could be used to identify the exact semi-circular canal with foreign otoconia causing the peripheral vestibular disruption. Compared to current diagnostic methodology, this determination could be made more accurately and without the need to provoke more symptoms of dizziness from the user at a later date.

In one or more embodiments, self-learning can help the system 10 become more useful to the user. For example, if certain head movements cause symptoms of dizziness to occur, the system 10 can provide real-time feedback that would discourage the user from making those movements. This type of conditioning could help users "learn their limits" until the condition has been treated and resolved. In one or more embodiments, machine learning can determine that the problem no longer exists and terminate the feedback being provided to the user.

In a similar way, detection of an episode among individuals who are known to suffer from Meniere's disease could allow the system 10 or a technician to make hearing assistance parameter adjustments. Reduction in hearing sensitivity is commonly a secondary symptom of Meniere's attacks and Endolymphatic hydrops. In these cases, the balance sensors could inform temporary increases in hearing aid gain. In one or more embodiments, these users can be given various memory settings with varying levels of amplification to allow for tuning adjustment during episodic fluctuations of hearing sensitivity.

In one or more embodiments, the controller 16 can also be adapted to determine the fall risk threshold by detecting the presence of alternating nystagmus and parameters of postural stability and inferring the level of intoxication of the user. For example, the consumption of alcohol or other chemical substances can result in periodic, alternating nystagmus, increased postural instability, and an increased risk for falling. Once a fall risk threshold is exceeded, a fall risk output such as a discrete audio alert may be provided to the user and, optionally, another threshold may be used to trigger an action which immobilizes the vehicle of the user. To further assist the user, during intoxication, the controller may be further adapted to arrange alternative modes of transportation on behalf of the user, such as arranging a ride share service pick-up or placing the vehicle into a self-driving mode, when the user attempts to operate the vehicle.

Figure 5:
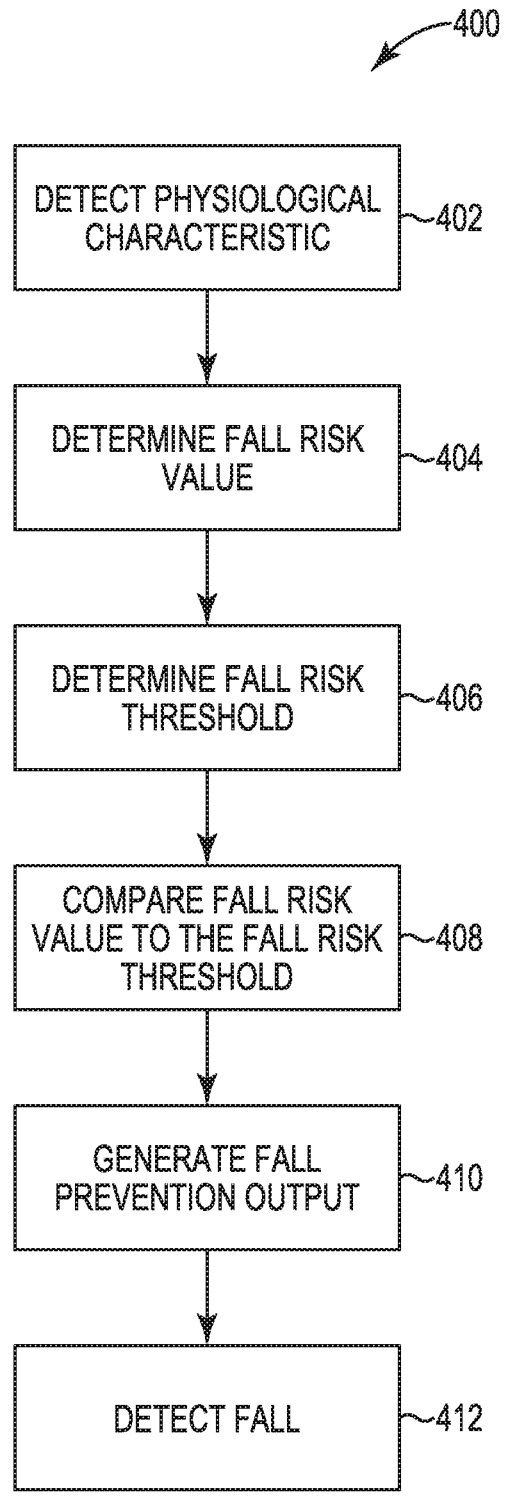
FIG. 5 is a flow chart of another embodiment of a method of utilizing the fall prediction system of FIG. 1.

As mentioned herein, any suitable technique or combination of techniques can be utilized with the fall prediction system 10 to determine the likelihood that the user will experience a fall or that the user has fallen. For example, FIG. 5 is a schematic flow chart of one embodiment of a method 400 that utilizes the system 10 of FIG. 1, which includes the hearing device 12 and the accessory 18. Although described in reference to the fall prediction system 10 of FIG. 1, the method 400 can be utilized with any suitable system or device. At 402, the characteristic of a user of the fall prediction system 10 can be detected with one or both of the sensor 14 and the accessory 18 using any suitable technique or techniques. Any suitable physiological characteristic of the user or of the environment proximate to the user (i.e., an environmental characteristic) can be detected at 402, e.g., a postural stability characteristic. In one or more embodiments, detecting the physiological characteristic includes detecting eye movement of the user using a first sensor and a second sensor each operatively connected to the hearing device, and generating an eye movement signal based on the detected eye movement.

A fall risk value based upon the detected characteristic or characteristics can be determined at 404. Any suitable technique or techniques can be utilized to determine the fall risk value. In one or more embodiments, determining the fall risk value includes detecting head movement of the user, generating a head movement signal based on the detected head movement, and comparing an eye movement signal to the head movement signal. At 406 a fall risk threshold can be determined using any suitable technique or techniques. Any suitable fall risk threshold can be determined at 406, e.g., a postural stability threshold.

Further, at 408 the fall risk value can be compared to the fall risk threshold. In one or more embodiments, a fall prevention output can be generated if the fall risk value exceeds the fall risk threshold at 410. The fall prevention output generated at 410 can include any suitable output or outputs. In one or more embodiments, generating the fall prevention output includes transmitting at least one of the physiological characteristic, environmental characteristic, fall risk value, and fall risk threshold to one or more of a caregiver, a medical professional, and the user. Further, in one or more embodiments, generating the fall prevention output includes determining a therapy to be delivered to the user, and delivering the therapy to the user. In or more embodiments, the method 400 can include detecting a fall at 412. Any suitable technique or techniques can be utilized to detect a fall.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A fall prediction system, comprising:
   a first hearing device configured to be worn on or in a first ear of a user, the first hearing device comprising:
   a control circuit,
   a first microphone in electrical communication with the control circuit,
   an electroacoustic transducer for generating sound in electrical communication with the control circuit,
   a power supply circuit in electrical communication with the control circuit, and
   a hearing device sensor in electrical communication with the control circuit and adapted to detect a characteristic of the user and generate a hearing device sensor signal based on the characteristic, wherein the hearing device sensor comprises a first motion sensor, wherein the characteristic comprises at least one of eye movement and head movement of the user;
   a second hearing device configured to be worn on or in a second ear of a user, the second hearing device comprising a second motion sensor;
   an accessory operatively connected to the hearing device, wherein the accessory is configured to be worn or held by the user, the accessory comprising an accessory sensor adapted to detect the characteristic of the user and generate an accessory sensor signal based on the characteristic, the accessory sensor comprising an accessory microphone, wherein the accessory sensor is physically separate from the hearing device sensor; and
   wherein the control circuit is adapted to:
   compare the hearing device sensor signal with the accessory sensor signal to determine the accuracy of data being collected by the hearing device sensor;
   determine a short-term fall risk value based on the hearing device sensor signal;
   compare the short-term fall risk value to a short-term fall risk threshold;
   indicate that the user has fallen only if both the first motion sensor and the second motion sensor indicate a fall event; and
   generate a fall prevention output if the short-term fall risk value exceeds the short-term fall risk threshold.

2. The system of claim 1, wherein the controller is a component of the accessory.

3. The system of claim 1, further comprising a second sensor operatively connected to the hearing device and adapted to detect a second characteristic of the user and generate a second sensor signal based on the second characteristic, wherein the controller is adapted to determine the short-term fall risk value based on the sensor signal and the second sensor signal.

4. The system of claim 3, wherein the second sensor is a component of the accessory.

5. The system of claim 1, wherein the accessory comprises at least one of a TV streamer, wireless audio streaming device, cell phone or landline streamer, Direct Audio Input (DAI) gateway, auxiliary audio input gateway, telecoil/magnetic induction receiver, hearing device programmer, charger, smartphone, smart glasses, and wearable or implantable health monitor.

6. The system of claim 1, wherein the controller is further adapted to determine the short-term fall risk threshold based on one or more settings of the accessory.

7. The system of claim 1, wherein the fall prevention output comprises at least one of an audible, visual, and tactile signal provided to the user.

8. The system of claim 1, wherein the hearing device further comprises hearing assistance components disposed within a housing of the hearing device, wherein the hearing assistance components comprise the controller.

9. The system of claim 1, wherein the fall prevention output comprises a transmission to one or more of a caregiver, medical professional, or the user, the transmission including at least one of the characteristic, and the short-term fall risk value.

10. The system of claim 1, wherein the hearing device sensor is configured to detect a fall and the accessory sensor is configured to confirm whether the fall has occurred.

11. The system of claim 1, wherein the controller is further configured to collect physiological data from the hearing device sensor prior to a fall event and analyze the physiological data to determine a reason for the fall event.

12. The system of claim 1, wherein the accessory sensor is configured to:
    monitor an ambient acoustic environment to determine if an alarm is sounding; and
    for each alarm detected, send an alert to the user.

13. The system of claim 1, the hearing device further comprising a second sensor in electrical communication with the control circuit, the second sensor comprising an electrooculography (EOG) sensor configured to track eye movement of the user.

14. The system of claim 13, wherein the control circuit is configured to correlate positional data from the first sensor to eye movement data from the second sensor to detect peripheral vestibular asymmetry in the user.

15. The system of claim 1, wherein the accessory microphone is configured to monitor the ambient acoustic environment to determine if an alarm is sounding, and to alert the user upon sensing an alarm.

16. The system of claim 15, wherein the accessory sensor is configured to learn the sounds for multiple alarms and to issue a distinct alert to the user depending on which of the alarms are sounding.

17. The system of claim 1, wherein the controller is further adapted to:
determine a long-term fall risk value based on the hearing device sensor signal;
compare the long-term fall risk value to a long-term fall risk threshold; and
generate a fall prevention output if the long-term fall risk value exceeds the long-term fall risk threshold.

18. The system of claim 1, wherein the controller is further adapted to determine that the user has dropped one of the first hearing device or the second hearing device if only one of the first motion sensor and the second motion sensor indicates a fall event.

19. A fall prediction system, comprising:
a first hearing device configured to be worn on or in a first ear of a user, the first hearing device comprising:
a control circuit,
a first microphone in electrical communication with the control circuit,
an electroacoustic transducer for generating sound in electrical communication with the control circuit,
a power supply circuit in electrical communication with the control circuit, and
a hearing device sensor in electrical communication with the control circuit and adapted to detect characteristics of the user and generate a hearing device sensor signal based on the characteristics, wherein the hearing device sensor comprises a first motion sensor, wherein the characteristics comprise both a physiological characteristic of the user and an environmental characteristic;
a second hearing device configured to be worn on or in a second ear of a user, the second hearing device comprising a second motion sensor;
an accessory operatively connected to the hearing device wherein the accessory is configured to be worn or held by the user, the accessory comprising an accessory sensor adapted to detect at least one of the characteristics of the user and generate an accessory sensor signal based on at least one of the characteristics, the accessory sensor comprising an accessory microphone, wherein the accessory sensor is physically separate from the hearing device sensor; and
wherein the control circuit is adapted to:
compare the hearing device sensor signal with the accessory sensor signal to determine the accuracy of data being collected by the hearing device sensor;
determine a short-term fall risk value based on the hearing device sensor signal;
compare the short-term fall risk value to a short-term fall risk threshold;
indicate that the user has fallen only if both the first motion sensor and the second motion sensor indicate a fall event; and
generate a fall prevention output if the short-term fall risk value exceeds the short-term fall risk threshold.

20. A fall prediction system, comprising:
a first hearing device configured to be worn on or in a first ear of a user, the first hearing device comprising:
a control circuit,
a first microphone in electrical communication with the control circuit,
an electroacoustic transducer for generating sound in electrical communication with the control circuit,
a power supply circuit in electrical communication with the control circuit, and
a hearing device sensor in electrical communication with the control circuit and adapted to detect a characteristic of the user and generate a hearing device sensor signal based on the characteristic, wherein the hearing device sensor comprises a first motion sensor, wherein the characteristic comprises at least one of eye movement and head movement of the user;
a second hearing device configured to be worn on or in a second ear of a user, the second hearing device comprising a second motion sensor;
wherein the control circuit is adapted to:
determine a short-term fall risk value based on the hearing device sensor signal;
compare the short-term fall risk value to a short-term fall risk threshold;
indicate that the user has fallen only if both the first motion sensor and the second motion sensor indicate a fall event; and
generate a fall prevention output if the short-term fall risk value exceeds the short-term fall risk threshold.

* * * * *